(12) United States Patent
García et al.

(10) Patent No.: US 9,836,583 B2
(45) Date of Patent: Dec. 5, 2017

(54) AUTOMATED MEDICATION ADHERENCE SYSTEM

(71) Applicant: SILVERGENS INC., Canoga Park, CA (US)

(72) Inventors: César Manuel García, Surfside, FL (US); Bart Jan Wanders, Trabuco Canyon, CA (US); Philip Eugene Alei, Carlsbad, CA (US); Conrado Orlando Diaz, Camarillo, CA (US)

(73) Assignee: SILVERGENS INC., Canoga Park, CA (US)

( * ) Notice: Subject to any disclaimer, the term of this patent is extended or adjusted under 35 U.S.C. 154(b) by 23 days.

(21) Appl. No.: 15/073,096

(22) Filed: Mar. 17, 2016

(65) Prior Publication Data
US 2017/0270274 A1    Sep. 21, 2017

(51) Int. Cl.
*G07F 11/00*    (2006.01)
*G06F 19/00*    (2011.01)
(Continued)

(52) U.S. Cl.
CPC ........ *G06F 19/3462* (2013.01); *A61J 7/0069* (2013.01); *A61J 7/0076* (2013.01);
(Continued)

(58) Field of Classification Search
CPC ... G06F 19/3462; A61J 7/0069; A61J 7/0076; A61J 7/02; A61J 2205/50; G07F 11/54; G07F 17/0092
(Continued)

(56) References Cited

U.S. PATENT DOCUMENTS 2,630,245 A * 3/1953 Maier ............... A47F 1/03
                                                      221/264
4,782,980 A * 11/1988 Heimlich ........ B65D 83/0409
                                                      221/203
(Continued)

FOREIGN PATENT DOCUMENTS

| CA | 2907092 A1 | 9/2014 |
|----|------------|--------|
| CA | 2907315 A1 | 9/2014 |
| WO | 2014145274 A1 | 9/2014 |

OTHER PUBLICATIONS

PCT Written Opinion of the International Searching Authority; Applicant Silvergens, Inc.; International Application No. PCT/US2017/020959; dated Jun. 15, 2017.

*Primary Examiner* — Rakesh Kumar
(74) *Attorney, Agent, or Firm* — Hankin Patent Law, APC; Kevin Schraven; Lindsey Auerbach

(57) ABSTRACT

An automated medication adherence system. The automated medication adherence system may comprise: a housing, an electronic interface, a plurality of reservoirs, one or more sensors, and at least one pill delivery and lock-out module. The electronic interface is programmable to accept data relating to a medication, including at least one of a pill identify, a user identity, a dosage schedule, and a side effect. The electronic interface actuates rotation of a reservoir, which is configured to receive, store, and dispense pills, tablets, and capsules of various sizes accurately and precisely. The sensors monitor medication input and output, and alerts a user when medication has been dispensed and needs to be taken.

10 Claims, 19 Drawing Sheets

(51) Int. Cl.
  *G07F 17/00* (2006.01)
  *G07F 11/54* (2006.01)
  *A61J 7/00* (2006.01)
  *A61J 7/02* (2006.01)

(52) U.S. Cl.
  CPC ............. *A61J 7/02* (2013.01); *G07F 11/54* (2013.01); *G07F 17/0092* (2013.01); *A61J 2205/50* (2013.01)

(58) Field of Classification Search
  USPC .......................................................... 221/2
  See application file for complete search history.

(56) References Cited

U.S. PATENT DOCUMENTS

| | | | |
|---|---|---|---|
| 5,280,845 A * | 1/1994 | Leight | G07F 11/44 221/1 |
| 5,472,113 A | 12/1995 | Shaw | |
| 5,609,268 A * | 3/1997 | Shaw | A61J 7/0084 221/2 |
| 5,646,912 A | 7/1997 | Cousin | |
| 5,884,806 A | 3/1999 | Boyer | |
| 5,915,589 A | 6/1999 | Lim | |
| 5,971,594 A | 10/1999 | Sahai | |
| 6,018,289 A | 1/2000 | Sekura et al. | |
| 6,138,865 A | 10/2000 | Gilmore | |
| 6,145,697 A | 11/2000 | Gudish | |
| 6,263,259 B1 | 7/2001 | Bartur | |
| 6,304,797 B1 | 10/2001 | Shusterman | |
| 6,332,100 B1 | 12/2001 | Sahai et al. | |
| 6,427,865 B1 | 8/2002 | Stillwell | |
| 6,490,502 B2 | 12/2002 | Fellows et al. | |
| 6,510,962 B1 | 1/2003 | Lim | |
| 6,594,549 B2 | 7/2003 | Siegel | |
| 6,732,884 B2 * | 5/2004 | Topliffe | A61J 7/0481 221/10 |
| 6,988,634 B2 | 1/2006 | Varis | |
| 7,080,755 B2 | 7/2006 | Handfield | |
| 7,213,721 B2 | 5/2007 | Abdulhay et al. | |
| 7,359,765 B2 | 4/2008 | Varvarelis et al. | |
| 7,440,818 B2 | 10/2008 | Handfield | |
| 7,630,790 B2 | 12/2009 | Handfield | |
| 7,715,277 B2 | 5/2010 | De La Huerga | |
| 7,721,914 B2 | 5/2010 | Handfield | |
| 7,735,681 B2 | 6/2010 | Handfeld | |
| 7,735,683 B2 | 6/2010 | Handfield | |
| 7,743,923 B2 | 6/2010 | Conley | |
| 7,751,933 B2 | 7/2010 | Handfield | |
| 7,844,362 B2 | 11/2010 | Handfield | |
| 7,860,603 B2 | 12/2010 | Handfield | |
| 7,886,931 B2 | 2/2011 | Handfield et al. | |
| 7,908,030 B2 | 3/2011 | Handfield | |
| 7,909,207 B2 | 3/2011 | Handfield | |
| 7,917,246 B2 | 3/2011 | Handfield | |
| 7,949,426 B2 | 5/2011 | Handfield | |
| 7,996,105 B2 | 8/2011 | Handfield | |
| 7,996,106 B2 | 8/2011 | Earvin | |
| 8,027,748 B2 | 9/2011 | Handfield | |
| 8,060,246 B2 | 11/2011 | Berg | |
| 8,060,249 B2 | 11/2011 | Bear et al. | |
| 8,112,175 B2 | 2/2012 | Handfield | |
| 8,152,020 B2 | 4/2012 | Flowers et al. | |
| 8,195,330 B2 | 6/2012 | Coe | |
| 8,261,939 B2 * | 9/2012 | Knoth | B65B 5/103 221/103 |
| 8,386,275 B2 | 2/2013 | Chambers | |
| 8,560,117 B2 | 10/2013 | Handfield | |
| 8,712,587 B2 | 4/2014 | Handfield | |
| 8,727,180 B2 | 5/2014 | Zonana et al. | |
| 8,914,148 B2 | 12/2014 | Wagner | |
| 9,043,015 B2 * | 5/2015 | Ratnakar | A61J 7/02 700/236 |
| 9,412,216 B2 * | 8/2016 | Rudek | A61F 15/001 |
| 2005/0234430 A1 | 10/2005 | Mao et al. | |
| 2006/0071011 A1 * | 4/2006 | Varvarelis | A61J 7/0481 221/9 |
| 2006/0144846 A1 | 7/2006 | Varis | |
| 2009/0127275 A1 | 5/2009 | Choi et al. | |
| 2009/0281657 A1 * | 11/2009 | Gak | A61J 7/0481 700/242 |
| 2010/0318218 A1 * | 12/2010 | Muncy, Jr. | G06F 19/3462 700/220 |
| 2011/0042404 A1 * | 2/2011 | Koike | G07F 9/026 221/2 |
| 2011/0208352 A1 * | 8/2011 | Knoth | B65B 5/103 700/243 |
| 2011/0301747 A1 | 12/2011 | Chambers | |
| 2014/0097194 A1 | 4/2014 | Lai | |
| 2014/0131378 A1 | 5/2014 | Shih et al. | |
| 2014/0244033 A1 * | 8/2014 | Ucer | A61J 7/0481 700/237 |
| 2014/0277702 A1 * | 9/2014 | Shaw | G06F 19/3462 700/232 |
| 2014/0277710 A1 | 9/2014 | Akdogan et al. | |
| 2014/0326744 A1 * | 11/2014 | Ratnakar | A61J 7/02 221/1 |
| 2015/0012131 A1 | 1/2015 | Saltsov | |
| 2015/0039124 A1 | 2/2015 | Mistovich et al. | |
| 2015/0090733 A1 | 4/2015 | Park | |
| 2015/0291344 A1 | 10/2015 | MacVittie et al. | |

* cited by examiner

AUTOMATED MEDICATION ADHERENCE SYSTEM

FIELD OF USE

The present disclosure relates generally to the field of article dispensing, and more specifically, to an automated medication adherence system for use in user's home.

BACKGROUND

In 2010, there were 15.4 million Medicare beneficiaries over the age of 65 with four or more chronic conditions, of which 43% were hospitalized at least once during the year. Further, an estimated 39% of the elderly population has some type of disability (i.e., difficulty in hearing, vision, cognition, ambulation, self-care, or independent living). For a considerable number of individuals, these types of disabilities may make it difficult to adhere to a medication schedule.

Many of these individuals may depend on untrained volunteers, family, or friends to help them manage their medications. Current estimates state there are 34.2 million Americans that have provided unpaid care to an adult 50 years old or over. Approximately a quarter of these caregivers provide 41 or more hours of care per week, typically for a close relative who has been hospitalized in the past year. These caregivers often experience stress, physical and financial strain, and adverse impacts on their health while they perform complex medical and nursing responsibilities.

Furthermore, the U.S. Census Bureau anticipates population growth of 60% for the age group over 65 years old and a population decline of 1% in the age group 45 to 64 years old between 2014 and 2030. This major demographic shift may significantly affect the support system for the elderly. Even individuals that receive assistance from a paid home health aide may still have issues managing their medications, as the majority of home health aides do not administer medication or provide assistance with self-administration of medications. Many of these home health aides are prohibited to administer medication by state law, or have not obtained the required medication technician certification required by most nurse delegation programs due to cost and potential liability concerns.

Even though the elderly currently comprise only 12% of the population, they consume 33% of all prescription drugs with two out of five Medicare beneficiaries taking five or more prescription medications. The large number of medications prescribed to the elderly and chronically ill, combined with the cognitive and sometimes physical challenges of following multiple medication regimens, reduce a patient's ability to fully benefit from prescribed medications. It has been estimated that 20-30% of medication prescriptions are never filled and 50% of the time medication is not continued and completed as prescribed. Polypharmacy, defined as taking multiple medications concurrently to treat coexisting diseases, with the elderly typically leads to medication non-adherence and is estimated to occur among 25%-75% of elderly patients, with the rate of occurrence increasing in proportion to the number of drugs and daily dosages prescribed. Lack of medication adherence can result in disease progression, death and higher costs to the healthcare system. Furthermore, non-adherence was estimated to account for 10% of hospital admissions and 23% of nursing home admissions. The New England Healthcare Institute calculates non-adherence along with suboptimal prescribing, drug administration and diagnosis could result in up to $290 billion in losses annually in the US. Additionally, estimates report the effect of poor medication adherence results in approximately 125,000 deaths in the US annually.

There are a growing number of studies that have documented net savings associated with higher medication adherence across a range of common chronic conditions. One study demonstrated improved medication adherence might provide a net economic return for certain chronic conditions, including diabetes, hypertension, hypercholesterolemia and congestive heart failure. Consequently, the study noted increased adherence to drug therapy reduced a patient's need for medical services, including hospitalizations and emergency room visits.

However, independent management of drug administration is a relatively ineffective way to increase medication adherence. Seven-day pillboxes are probably the most common products used, but they require manual sorting of pills on a weekly basis. This is an unreliable and cumbersome process that sometimes requires assistance from a caregiver or pharmacist. One study noted that the majority of elderly patients may be unable to open and access their medications from multi-compartment pillboxes with ease, and cognitively impaired patients may experience even more difficulties than others. Forgetfulness is a major factor contributing to non-adherence, with an estimated 30% of patients with chronic conditions asserting forgetfulness. This poses a further challenge to independent seniors, which are at a higher risk of forgetting to take their medication if they experience increased busyness. However, most pillboxes do not provide interactive reminders or instructions, and are thus inadequate solutions in this respect. Another downside to pillboxes is that they may promote cross-contamination, as different pills are placed inside a small compartment together.

Smart phone applications have been developed to assist in medication adherence through reminders and alerts, but are not comprehensive solutions addressing the specific needs for patients with several chronic conditions and potentially suffering from physical and cognitive impairments. As a result, reminders and alarms alone are not likely to improve adherence unless they are designed to provide relevant information with interactive features to facilitate addressing these concerns on a timely basis. Lastly, there are mail order pharmacies that specialize in pre-sorting prescription pills into pill pouches or blister packs and shipping directly to patients. However, the process of managing medication changes is cumbersome and apt to wasting a supply of medication. Although the pre-sorted packets help to simplify the medication administration, this is clearly not an interactive system with real-time capability to remind, instruct, monitor, and alert the status of the patient's medication adherence record.

Currently, there are no medication adherence solutions on the market that are comprehensive, fully automated, and requires no programming by the user. In addition, critical information such as medication formularies, e-prescriptions and pharmaceutical databases are kept in "silos" and are not readily available in an integrated fashion, making it difficult to retrieve data for contextual analysis. Consequently, even the more advanced medication administration products on the market still require manual pill sorting and programming of alarms and reminders—a challenging task for this at-risk population.

Accordingly, there exists a need for a device that provides an effective solution for both patients and health care providers regarding the patient's adherence or compliance with complicated medication regimens. In particular, there exists a need for an automated medication adherence system to help organize the dispensing of many different sizes and shapes of pills and capable of managing a schedule of different pills to be taken at different scheduled times. Such a system should enhance the interaction between the patient and health care provider by allowing the health care provider to be alerted when the patient is not taking the medication according to the medication schedule.

SUMMARY

To minimize the limitations in the cited references, and to minimize other limitations that will become apparent upon reading and understanding the present specification, the present specification discloses a new and improved automated medication adherence system.

One embodiment may be an automated medication adherence system, comprising a housing and an electronic interface. The electronic interface may use such data to automatically program the control logic for operating the electromechanical operation of the adherence system and the medication dispensing and scheduling functions using information from pharmacy prescription records, pharmaceutical databases and medical professionals. The electronic interface acquires data to schedule, alert and record therapies for pill and non-pill medications. The housing may comprise a medication dispensing and lock-out module. The housing may be configured to contain a plurality of reservoirs wherein the plurality of reservoirs may be configured for receiving, storing, and dispensing one or more medications. The housing may comprise an access cover configured to have closed and opened position. The plurality of reservoirs may be accessible when the access cover is in the opened position. The access cover may comprise a pill loading assembly wherein the pill loading assembly may be configured to allow one or more medications to be loaded into at least one of the plurality of reservoirs. The electronic interface may comprise a computing component and multiple display components. The electronic interface may be on an exterior portion of the housing. The electronic interface may be programmable, such that the electronic interface accepts data relating to one or more medications from pharmacies, medical professionals, database companies and other authorized users. Each of the plurality of reservoirs may be configured to receive, store and dispense a homogenous type of medication from the one or more medications. Each of the plurality of reservoirs may comprise one or more sensors and two successive stages, a first stage and a second stage. The one or more medications may be moved from the first stage to the second stage and then from the second stage to the pill delivery and lock-out module. The one or more medications may be a plurality of pills. The one or more sensors may be configured to determine when a single pill of the plurality of pills passes through each of the two successive stages and may control pill ejection from stage 1 or 2, as appropriate. The automated medication adherence system may further comprise a rotating carrier configured to engage with the plurality of reservoirs, such that the plurality of reservoirs may be configured to rotate within the housing. The electronic interface may rotate the plurality of reservoirs in response to the data relating to the one or more medications. The data relating to the one or more medications may be selected from the group of data gathered or created through manipulation of data from prescription records, pharmaceutical databases and proprietary data bases consisting of information such as: a pill identity; a user identity; a dosage schedule; medication format (pill or non-pill; such as inhalers, solutions, creams, etc.), pill images, pharmaceutical indications for use, instructions (directions) for use, physical and chemical description of the medications, refills, side effect information and other information customarily used to manage and administer medications. The two successive stages may be configured to be stacked, such that the first stage may be substantially above the second stage. Each of the two successive stages may comprise an opening, such that there are two openings, a first opening and a second opening. The first opening and the second opening may be selectively openable and closable in response to the electronic interface. Each of the two successive stages may receive and dispense the one or more medications through the two openings. Each of the plurality of reservoirs may comprise a central agitation stalk, an outer wall; an inner wall; optionally one or more actuators and sensors. The central agitation stalk may be configured to be substantially contained within the inner wall, and the inner wall may be configured to be substantially contained within the outer wall. The central agitation stalk may be configured to be rotatable within the inner wall. The central agitation stalk may comprise a fin portion, a wave surface, and a ribbed cone surface. The fin portion may comprise a plurality of fins that may be configured to prevent the one or more medications from clumping together. The wave surface may be a base of the first stage; and the ribbed cone surface may be a base of the second stage. The ribbed cone may have ribs, undercuts, channels or any type of texture or geometry suitably to transport the pills to the stage 2 opening. A combination of wave surface and the ribbed cone can be used at both stage 1 and stage 2. The one or more actuators may be configured to rotate and agitate the central agitation stalk and at least one of the inner wall and the outer wall. The outer wall may comprise one or more outer wall portholes and one or more chutes. The inner wall may comprise one or more inner wall portholes. At least one of the one or more actuators may be configured to rotate at least one of the inner wall and the outer wall, such that the inner wall and they outer wall may be rotated with respect to each other. When the inner wall and the outer wall are rotated with respect to each other, the one or more outer wall portholes and the one or more inner wall portholes may align to form the two openings that best match the solid geometry of the pill in that reservoir. The computing component may comprise one or more logic algorithms. The one or more sensors, the one or more actuators, and the one or more logic algorithms may be configured to control the inner wall, the outer wall, and the central agitation stalk to ensure that the one or more medications may be transferred, one pill at a time, from the first stage to the second stage. The one or more sensors, the one or more actuators, and the one or more logic algorithms may be configured to control the inner wall, the outer wall, and the central agitation stalk to ensure that the one or more medications may be transferred, one pill at a time, from the second stage to the pill delivery and lock-out module. The electronic interface may alert a user when the one or more medications are dispensed, such that a dispensed medication may be created. The electronic interface may also alert a user when the one or more non-pill medications are required. The electronic interface may alert the user, one or more authorized individuals, and/or one or more health care providers when a user has not removed the dispensed medication from the pill delivery and lock-out module in accordance with the data relating to the one or more medications. The pill delivery and lock-out module may comprise three functions created by the translation of a pill transporter. The pill transporter may create a holding tray, a dispensing tray and a lock-out tray depending on the position of the pill transporter. If the pill transporter is in the neutral position, below the reservoir, it holds the pill or plurality of pills dispensed creating a holding tray. The transporter moves forward to create and form a pill dispensing tray that opens toward the user when the user is ready to take the pills. If the pills are not removed by the patient after a predetermined or calculated amount of time, or erroneously dispensed, the pill transporter may move in reverse to transfer the pills to a lock-out tray.

Another embodiment of the automated medication adherence system may comprise: a housing; an electronic interface; and a rotating carrier. The housing may comprise a pill loading assembly and a pill delivery and lock-out module. The housing may be configured to contain a plurality of reservoirs. The plurality of reservoirs may be configured for receiving, storing, and dispensing one or more medications. The rotating carrier may be configured to engage with the plurality of reservoirs, such that the plurality of reservoirs may be configured to rotate within the housing. The housing may comprise an access cover configured to have a closed and an opened position typically used for set-up and maintenance. The housing may comprise a reservoir loading door configured to have a closed and an opened position to be accessed by the end user. The plurality of reservoirs may be accessible when the access cover or the reservoir loading door are in the opened position. The reservoir loading door may comprise a reservoir loading assembly configured to allow the plurality of reservoirs to be loaded. The electronic interface may comprise a computing component and one or more display components. The user interface portion of the electronic interface may be on an exterior portion of the housing. The electronic interface may be manually programmed by the user or automatically by accepting data relating to the one or more medications, prescriptions, and prescription processes (e.g. refills, medication changes). The data relating to the one or more medications may be selected from the group of data from pharmacy prescription records, providers prescription records, pharmaceutical databases or proprietary databases consisting of: a pill identity; a user identity; a dosage schedule; medication format (pill or non-pill; such as inhalers, solutions, creams, etc.), pharmaceutical indications for use, instructions (directions) for use, physical and chemical description of the medications, pill images, instruction for use, refills, side effect information and other information customarily use to manage and administer medications. The electronic interface may rotate the plurality of reservoirs in response to the data relating to the one or more medications. Pills may be loaded through the pill loading assembly. Each of the plurality of reservoirs may be configured to receive, store and dispense a homogenous type of the medication. Each of the plurality of reservoirs may comprise one or more sensors and two successive stages, a first stage and a second stage. The medication may be moved from the first stage to the second stage and then from the second stage to the pill delivery and lock-out module. The two successive stages may be configured to be stacked, such that the first stage may be substantially above the second stage. Each of the two successive stages may comprise an opening, such that there may be two openings, a first opening and a second opening. The first opening and the second opening may be selectively openable and closable in response to the electronic interface. Each of the two successive stages may receive and dispense the medication through the two openings. The medication may be a plurality of pills. The one or more sensors may be configured to determine when a single pill of the plurality of pills passes through each of the two openings and triggers the immediate closing of the opening. Each of the plurality of reservoirs may comprise a central agitation stalk, an outer wall, an inner wall, and one or more actuators. The central agitation stalk may be configured to be substantially contained within the inner wall, and wherein the inner wall may be configured to be substantially contained within the outer wall. The central agitation stalk may be configured to be rotatable within the inner wall. The central agitation stalk may comprise a fin portion, a wave surface, and a ribbed cone surface. The fin portion may comprise a plurality of fins that may be configured to prevent the medication from clumping together. The wave surface may be a base of the first stage. The ribbed cone surface may be a base of the second stage. The central agitation stalk may be configured to engage with at least one of the one or more actuators in order to be rotated. The central agitation stalk may comprise a plurality of gear teeth, which may be configured to be engaged with at least one of the one or more actuators. The one or more actuators may be configured to rotate the central agitation stalk and at least one of the inner wall and the outer wall. The one or more actuators may be configured to rotate or agitate the central agitation stalk and at least one of the inner wall and the outer wall. The outer wall may comprise one or more outer wall portholes and one or more chutes. The inner wall may comprise one or more inner wall portholes. At least one of the one or more actuators may be configured to rotate at least one of the inner wall and the outer wall, such that the inner wall and the outer wall may be rotated with respect to each other. When the inner wall and the outer wall are rotated with respect to each other, the one or more outer wall portholes and the one or more inner wall portholes may align to form the two openings. The computing component may comprise one or more logic algorithms. The one or more sensors, the one or more actuators, and the one or more logic algorithms may be configured to control the inner wall, the outer wall, and the central agitation stalk to ensure that the medication may be transferred, one pill at a time, from the first stage to the second stage. The one or more sensors, the one or more actuators, and the one or more logic algorithms may be configured to control the inner wall, the outer wall, and the central agitation stalk to ensure that the medication may be transferred, one pill at a time, from the second stage to the pill delivery and lock-out module. The one or more logic algorithms may be configured to schedule and control the dispensing of medication according to the corresponding prescription or plurality of prescriptions and instructions for use.

Another embodiment of the medication reservoir for an automated medication adherence system may comprise two successive stages, a first stage and a second stage. The reservoir may be configured for receiving, storing, and dispensing a plurality of pills. Dispensing of the plurality of pills by the reservoir may be controlled by an electronic interface. The plurality of pills may be moved from the first stage to the second stage one pill at a time. The plurality of pills may be moved from the second stage to a pill delivery and lock-out module one pill at a time. Each of the two successive stages may comprise an opening, such that there may be two openings, a first opening and a second opening. The medication reservoir may further comprise one or more sensors wherein the one or more sensors may be configured to determine when a single pill of the plurality of pills passes through each of the two openings. The first and second openings may be selectively openable and closable in response to the electronic interface. The two successive stages may be configured to be stacked, such that the first stage may be substantially above the second stage. The reservoir may further comprise a central agitation stalk, an outer wall, an inner wall, and one or more actuators. The central agitation stalk may be configured to be substantially contained within the inner wall, and the inner wall may be configured to be substantially contained within the outer wall. The central agitation stalk may be configured to be rotatable within the inner wall. The central agitation stalk may comprise a fin portion, a wave surface, and a ribbed cone surface. The fin portion may comprise a plurality of fins that may be configured to prevent the one or more medications from clumping together. The wave surface may be a base of the first stage and the ribbed cone surface may be a base of the second stage. The one or more actuators may be configured to rotate and agitate the central agitation stalk and at least one of the inner wall and the outer wall. The outer wall may comprise one or more outer wall portholes and one or more chutes. The inner wall may comprise one or more inner wall portholes. At least one of the one or more actuators may be configured to rotate at least one of the inner wall and the outer wall, such that the inner wall and the outer wall may be rotated with respect to each other. The inner wall and the outer wall may be rotated with respect to each other, the one or more outer wall portholes and the one or more inner wall portholes may align to form the two openings. The electronic interface may comprise one or more logic algorithms. The one or more sensors, the one or more actuators, and the one or more logic algorithms may be configured to control the inner wall, the outer wall, and the central agitation stalk to ensure that the one or more medications may be transferred, one pill at a time, from the first stage to the second stage. The one or more sensors, the one or more actuators, and the one or more logic algorithms may be configured to control the inner wall, the outer wall, and the central agitation stalk to ensure that the one or more medications may be transferred, one pill at a time, from the second stage to the pill delivery and lock-out module.

It is an object to provide an automated medication adherence system to schedule medication dosage, medication replenishment, medication stoppage, and treatment changeovers with minimal user intervention.

It is an object to provide an automated medication adherence system with the ability to dispense a prescribed medication with an accuracy of up to 1:100,000.

It is an object to provide an automated medication adherence system to safely manage frequent changes in medication treatment and many different sizes of pills.

It is an object to provide an automated medication adherence system to provide error-free medication loading by a patient with potential physical and cognitive limitations.

It is an object to provide an automated medication adherence system with mechanical pill handling that does not affect the integrity of the medication.

It is an object to provide an automated medication adherence system capable of acquiring and communicating prescription instructions.

It is an object to provide ease of use by enabling a system that uses a single type of reservoir that can be programmed to handle pills of all sizes, solid geometries and construction methods. The reservoir can be used at any position within the rotating carrier.

It is an object to provide and record "pro re nata" (on demand or as needed) medication events to patients, if required.

It is an objective to provide maximum patient safety avoiding over-dosage or wrong dosage or wrong medication).

It is an object to overcome the limitations of the prior art.

Other features and advantages will become apparent to those skilled in the art from the following detailed description and its accompanying drawings.

BRIEF DESCRIPTION OF THE DRAWINGS

The drawings show illustrative embodiments, but do not depict all embodiments. Other embodiments may be used in addition to or instead of the illustrative embodiments. Details that may be apparent or unnecessary may be omitted for the purpose of saving space or for more effective illustrations. Some embodiments may be practiced with additional components or steps and/or without some or all components or steps provided in the illustrations. When different drawings contain the same numeral, that numeral refers to the same or similar components or steps.

DETAILED DESCRIPTION OF ILLUSTRATIVE EMBODIMENTS

In the following detailed description of various embodiments, numerous specific details are set forth in order to provide a thorough understanding of various aspects of the embodiments. However, the embodiments may be practiced without some or all of these specific details. In other instances, well-known procedures and/or components have not been described in detail so as not to unnecessarily obscure aspects of the embodiments.

While some embodiments are disclosed here, other embodiments will become obvious to those skilled in the art as a result of the following detailed description. These embodiments are capable of modifications of various obvious aspects, all without departing from the spirit and scope of protection. The Figures, and their detailed descriptions, are to be regarded as illustrative in nature and not restrictive. Also, the reference or non-reference to a particular embodiment shall not be interpreted to limit the scope of protection.

In the following description, certain terminology is used to describe certain features of one or more embodiments. For purposes of the specification, unless otherwise specified, the term "substantially" refers to the complete or nearly complete extent or degree of an action, characteristic, property, state, structure, item, or result. For example, in one embodiment, an object that is "substantially" located within a housing would mean that the object is either completely within a housing or nearly completely within a housing. The exact allowable degree of deviation from absolute completeness may in some cases depend on the specific context. However, generally speaking, the nearness of completion will be so as to have the same overall result as if absolute and total completion were obtained. The use of "substantially" is also equally applicable when used in a negative connotation to refer to the complete or near complete lack of an action, characteristic, property, state, structure, item, or result.

As used herein, the terms "approximately" and "about" generally refer to a deviance of within 5% of the indicated number or range of numbers. In one embodiment, the term "approximately" and "about", may refer to a deviance of between 1-10% from the indicated number or range of numbers.

Figure 1:
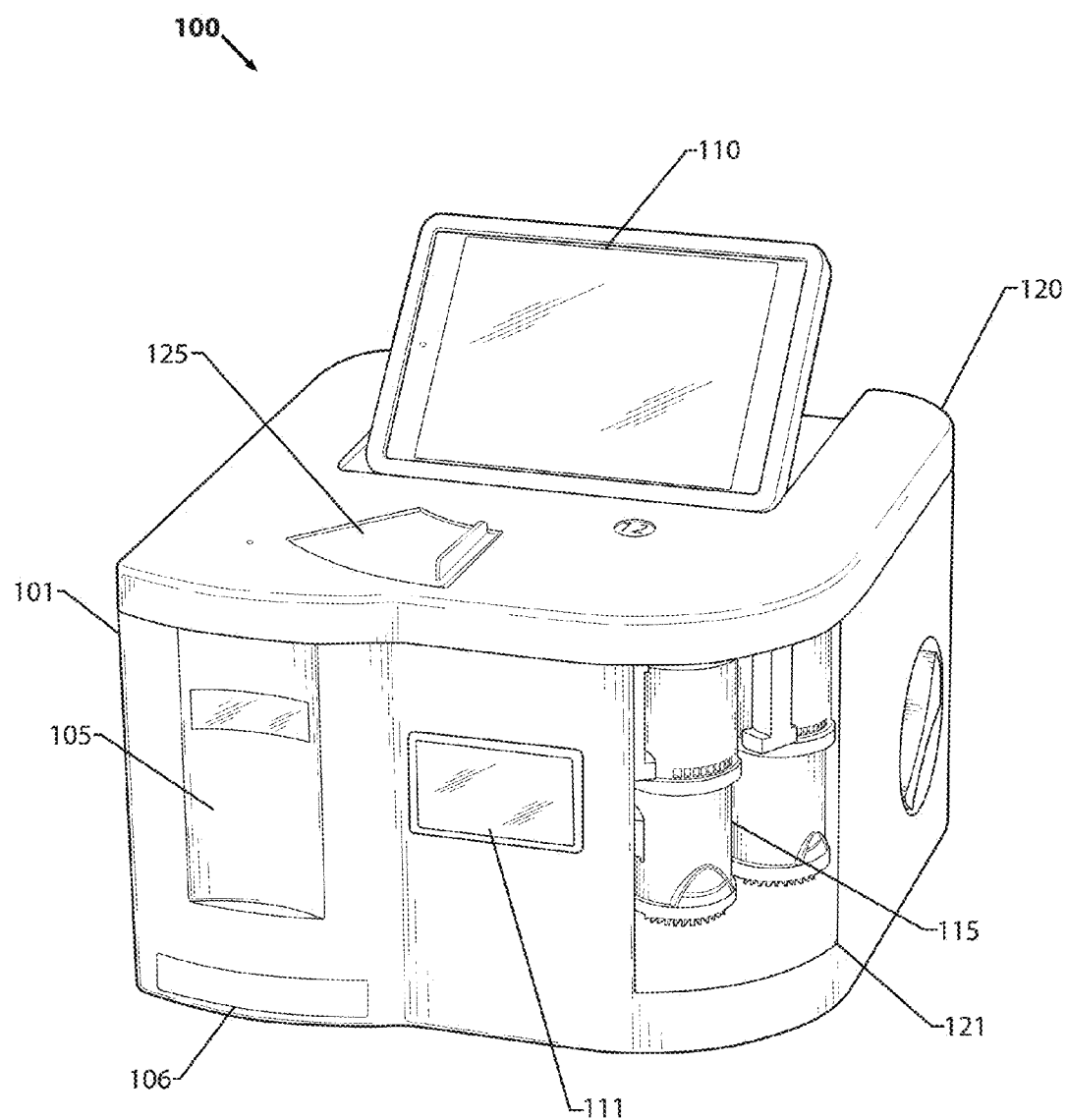
FIG. 1 is an illustration of a perspective view of one embodiment of the automated medication adherence system.

FIG. 1 is an illustration of a perspective view of one embodiment of the automated medication adherence system. As shown in FIG. 1, one embodiment of the automated medication adherence system 100 may comprise: a housing 101, a bar code reader 105, electronic interfaces 110, 111 a plurality of reservoirs 115, one or more sensors (shown in FIG. 6), and at least one pill delivery and lock-out module 106. The housing 101 may be any suitable shape and size for containing one or more reservoirs 115. For example, the housing 101 may be cubed shaped, as shown in FIG. 1. The housing 101 may define an exterior and an interior of the automated medication adherence system 100. The exterior may comprise a bottom surface that is capable of supporting the automated medication adherence system 100 on a flat surface, such as a desk or countertop. The exterior may comprise a top access cover 120, hereinafter referred to as an access cover, and a reservoir loading door 121 (shown in FIG. 13). The access cover 120 may be movable to an open position for manually placing reservoirs 115 into the interior or removing the reservoirs 115 or to maintain the system. The access cover 120 may preferably be movable to a closed and lockable position for preventing manual access to the reservoirs 115. Preferably, the reservoir loading door 121 may be used to load or remove reservoirs 115 by the end user. The lockable reservoir loading door 121 may be movable to an open position for manually placing or removing reservoirs 115 into the interior or removing the reservoirs 115 one at a time. Theft of prescription medicines by relatives of the prescription holder may be a problem solved by locking the access cover 120 and reservoir loading door 121. When the access cover 120 is in a closed lockable position, a pill loading assembly 125 located on at least one portion of the access cover 120 may provide access between the exterior of the housing 101 and the interior of the housing 101 in order to load medication into the reservoirs 115. Typically, gravity may be used to assist in loading medication through the pill loading assembly 125 into the reservoirs 115. The interior of the housing 101 may form an interior space that is sufficiently large to completely enclose the structural components of the automated medication adherence system 100. There may preferably be twelve reservoirs 115, which may preferably house at least sixty (60) of the largest prescribed pills each. A movable carrier, hereinafter referred to as a rotating carrier, may hold the reservoirs 115 in position wherein the electronic interfaces 110, 111 may actuate a motor to rotate the rotating carrier in order to align a pre-determined reservoir 115 with the pill loading assembly 125 of the access cover 120, such that medication may travel through the pill loading assembly 125 and into the correct, known, and identified reservoir 115. The rotating carrier may then rotate again to allow a user to load additional medications into different reservoirs 115. Each reservoir 115 may preferably house a homogenous type of medication, but this single type of medication may be one of many different sizes or shapes. The reservoirs 115 may comprise a medication preservation system to avoid cross-contamination, such as ultraviolet light protection, dust, excessive humidity, lids, and/or removable films. Additionally, in order to prevent contamination, a new reservoir 115 may be used each and every time a new medication is loaded and the medication may not contact or reuse any conduit except the pill loading assembly 125 of the access cover 120 and the pill delivery and lock-out module 106.

The reservoirs 115 are preferably configured to isolate a dosage of the medication contained in the specific reservoir 115 and then automatically deliver the dosage to the pill delivery and lock-out module 106. The dosage may be one pill or more than one pill, depending on the prescription. The system may repeat the dispensing process if multiple pills of the same type are simultaneously required. Preferably the rotating carrier rotates, such that the appropriate reservoir 115 is next to the pill delivery and lock-out module 106. The reservoir 115 may then deliver the dosage to the pill delivery and lock-out module 106. The rotating carrier may then rotate again, such that the next reservoir 115 may deliver a dosage of a different pill type. Once all of the dosages for that dosage time period have been delivered, the user may then take the dosage from the pill delivery and lock-out module 106. Under certain circumstances, it may be recommendable to deliver one pill type at a time, instead of all pills scheduled at the same time. The system algorithms may be capable to handle these instructions for use.

The housing 101 of the automated medication adherence system 100 may have a pill delivery and lock-out module 106, which may be a drawer, door, swing door, chute, and/or tray. The pill delivery and lock-out module 106 may be open or may be a locked portion, which is only unlocked for the specific user at a specific time. Once the entire dosage is in the pill delivery and lock-out module 106, the automated medication adherence system 100 may preferably notify the user to retrieve the dosage. This notification may be an audible alert, visual alert, vibration, and/or a wireless electronic communication to an electronic device used by the user. The pill delivery and lock-out module 106 may have one or more sensors that determine the status of the dosages within the pill delivery and lock-out module 106. The pill delivery and lock-out module 106 opens to deliver medications to user.

The pill delivery and lock-out module 106 may comprise a lock-out tray that opens in the event that a dosage is not removed from the dispensing tray configuration of the pill delivery and lock-out module 106 by the user. In this manner, the next dosage does not get mixed up with the missed dosage, avoiding an overdose. The system may record all medication events and a high frequency of pills transferred to the lock-out module may constitute a pattern of non-adherence. Preferably, if medication non-adherence becomes an issue, a notification may be sent to the user, pharmacy, care giver and/or a health care provider. In this manner, non-adherence can be dealt with appropriately.

Although a rotating carrier is shown as the mechanism that moves the reservoirs 115 within housing 101, the motion of the reservoirs 115 may be accomplished by other devices, including actuators, pulleys, slides, and the like.

A bar code reader 105 may be positioned on the exterior of the housing 101, or at another appropriate location, to read the medication prescription record number and other bar-coded information needed for automatic programming and ease of use by a user of the automated medication adherence system 100. For example, the bar code reader 105 may enable the recognition of data relating to the medication, including a pill identity, pill type, pill size, pill shape, a user identity, a dosage schedule, dosage information, and potential side effects that may be used to automatically program the automated medication adherence system. Therefore, the automated medication adherence system 100 does not require any programming by a user. Prior to loading medication into a reservoir 115, the bar code reader 105 may allow the user to send the data relating to the medication to the electronic interface 110 for programming each of the reservoirs 115 with the specific information required to accurately dispense the medication to be loaded.

Likewise, the electronic interfaces 110, 111 may be positioned on the exterior of the housing 101, or at another appropriate location, for ease of use by a user of the automated medication adherence system 100. FIG. 1 shows that the electronic interfaces may be a permanent fixture and/or a removable hand held computing device. The electronic interfaces 110,111 may be used for accomplishing various interface and notification functions. For example, the electronic interface 110,111 may also be manually programmed with data relating to the medication, including a pill identity, pill type, pill size, pill shape, pill images, schedule time, daily frequency, a user identity, a dosage schedule, dosage information, not to exceed amounts, instructions for use and potential side effects. The electronic interfaces 110,111 may enable programming of each of the reservoirs 115 with the specific information about the medication to be held in the respective reservoir 115. The electronic interface may facilitate the openings, agitation, and rotational parameters of each reservoir 115 to match the geometry, size and construction of each pill type so each reservoir 115 may be capable of accurately dispensing any pill type. The electronic interfaces 110, 111 may comprise a computing component and a display/interactive component. The computing component may control the one or more reservoirs 115, such that the precise dosage of medication is delivered from the reservoirs 115 to the pill delivery and lock-out module 106 each and every time on the dosage schedule. The display/interactive components may preferably be a touch screen so the patient can acknowledge and authorize certain steps, initiate certain actions, and provide a high level of interactivity and operability.

Figure 2:
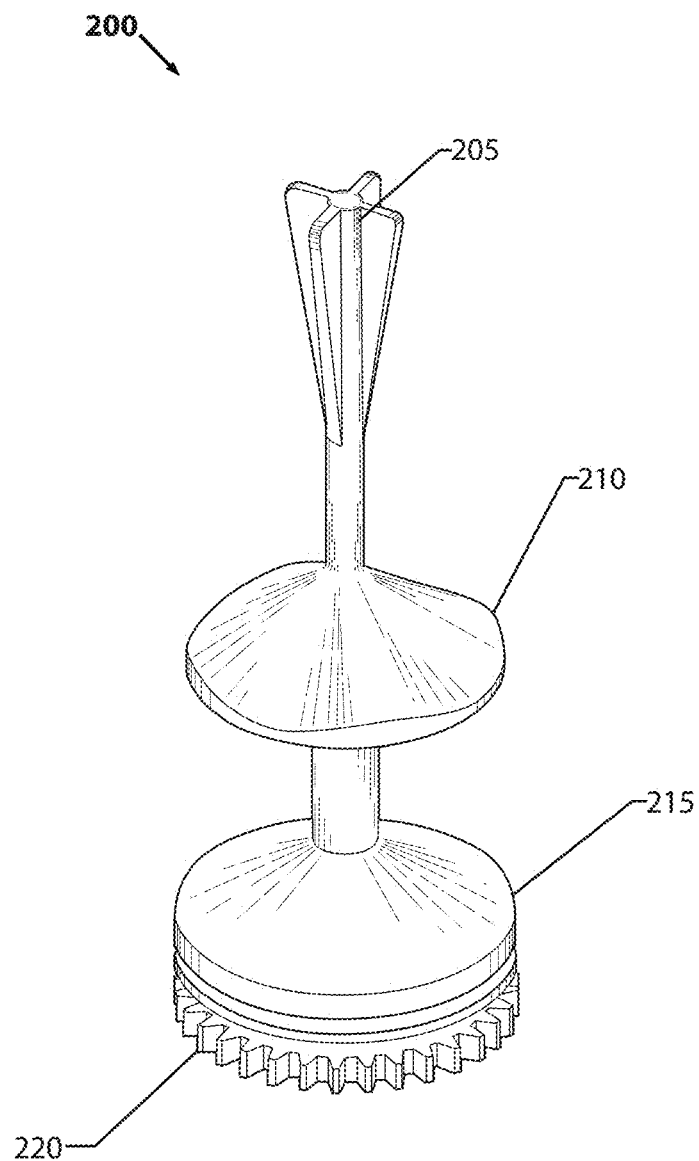
FIG. 2 is an illustration of a perspective view of one embodiment of a central agitation stalk.

FIG. 2 is an illustration of a perspective view of one embodiment of a central agitation stalk for the reservoirs. FIG. 2 shows that each reservoir within the automated medication adherence system may comprise a central agitation stalk 200. The central agitation stalk 200 may generally provide rotation and agitation within the reservoir, such that each reservoir may receive, store, and dispense pills, tablets, and capsules of various sizes and geometries accurately and precisely. The central agitation stalk 200 may comprise fin portion 205, a wave surface 210, a ribbed cone surface 215, and gear teeth 220. When a user loads medication into a reservoir, the fin portion 205 may prevent the medication from inadvertently clumping together. The medication may generally fall onto the wave surface 210 and be stored until the electronic interface causes the reservoir to dispense the medication. At a desired and/or scheduled time period, a drive mechanism engages with gear teeth 220 and causes the central agitation stalk 200 to rotate in order to move the medication on the wave surface 210. This rotational movement may be combined with an agitation movement in order to move—one pill at a time—the medication from the first stage (wave surface 210) to the lower or second stage (ribbed cone surface 215). The medication may reside on the ribbed cone surface 215 until it is ready to be dispensed, one pill at a time, into a pill delivery and lock-out module. The fin portion 205, wave surface 210, and ribbed cone surface 215 may be rotated and/or agitated simultaneously, or separately, such that only one or two rotate, while the others remain still.

Figure 3:
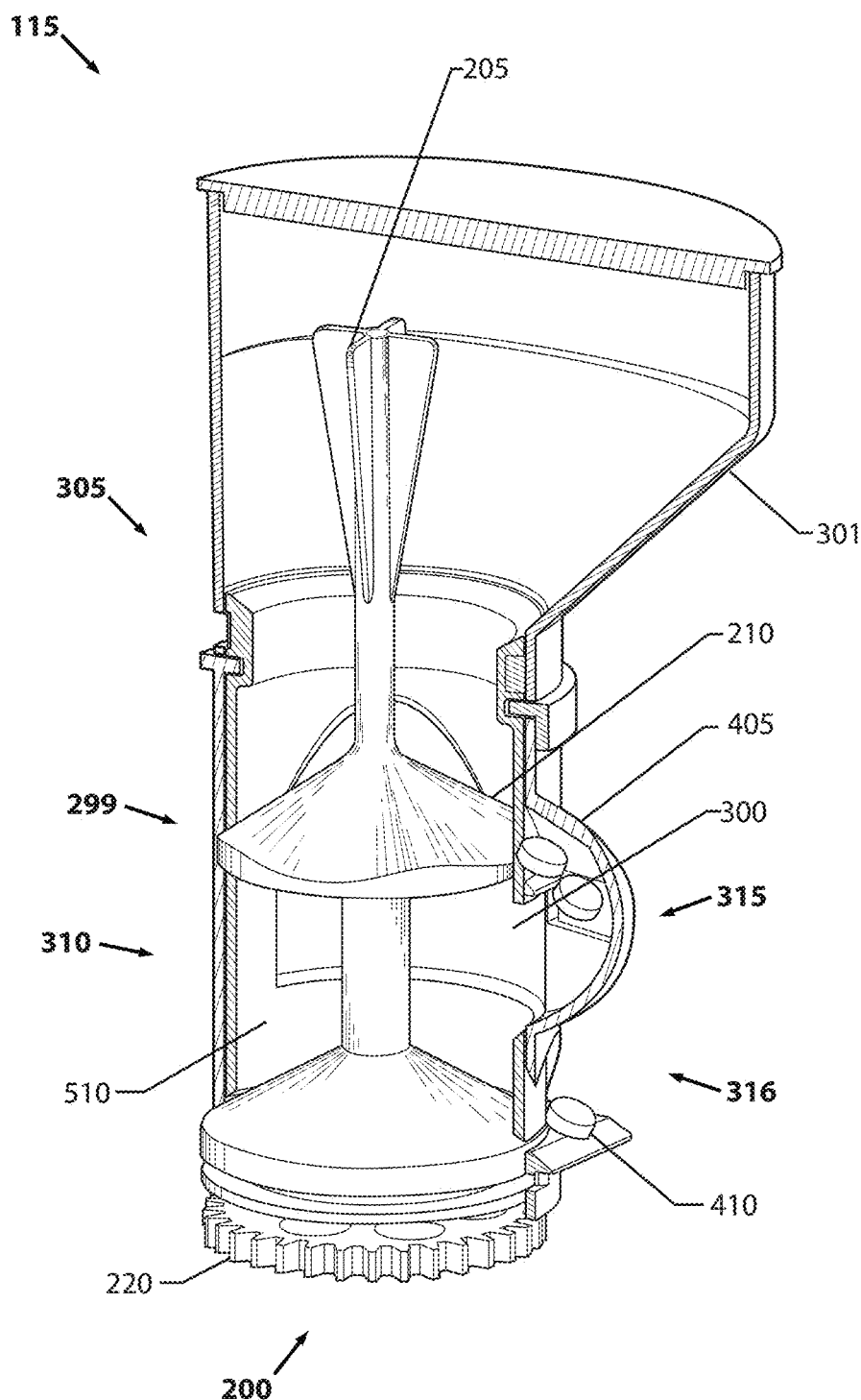
FIG. 3 is an illustration of a cross-section view of one embodiment of a reservoir that is contained within the automated medication adherence system.

FIG. 3 is an illustration of a cross-section view of one embodiment of a reservoir that is contained within the automated medication adherence system. FIG. 3 shows that each reservoir 115 within the automated medication adherence system may comprise a generally cylindrical two-stage device for storing and dispensing medication. The cylindrical reservoir 115 may comprise a stalk housing 299, also referred to as a reservoir housing, and a central agitation stalk 200. As shown in FIG. 3, the stalk housing 299 may comprise a funnel shaped hopper 301 and two overlapping walls, outer 300 and inner wall 510. The central agitation stalk 200, inner wall 510, and outer wall 300 may delineate the boundaries of the first stage 305 and the second stage 310. The first stage 305 may comprise a receptacle for storing medication, and then transfer the medication, in a controlled manner, to the second stage 310. Once the reservoir 115 to be loaded with medication is aligned with the pill loading assembly in the access cover, a user may load medication via the top of the reservoir 115 into the first stage 305 of the reservoir 115. FIG. 3 shows that the hopper 301 may be wide and funnel shaped in order to allow loading of the medication through the access cover without spilling any pills or medication and to maximize storage capacity. The medication may fall past the fin portion 205 and the central agitation stalk 200 may rotate in order for the medication to settle onto the wave surface 210. The first stage 305 may also comprise a first opening 315 around the periphery such that the medication may exit the first stage 305 and enter the second stage 310. Sensors, rotational and agitation actuators, and logic algorithms may ensure that only a specified number of pills, usually one or two pills, are transferred— one pill at a time—from the first stage 305 to the second stage 310. The second stage 310 may comprise a second opening 316 for allowing the medication to be dispensed, one pill at a time, to the pill delivery and lock-out module. The first and second openings 315, 316 may be created when openings in the inner and outer walls 510, 300 overlap through rotational motion to create an opening that best matches the pill geometry. Proprietary algorithms may use information from the pharmacy prescription records and pharmaceutical and/or proprietary databases to calculate the reservoir 115 openings 315, 316 and certain agitation and rotation parameters required to dispense the pills with high degree of accuracy. FIG. 3 also shows that the openings 315, 316 may comprise or be connected to chutes 405 and 410. As the medication pill passes through openings 315 or 316, the chutes 405, 410 may direct it to travel along a predetermined path.

In other embodiments, the stalk 200 housing may be of a unitary design, wherein rotational, actuation, and agitation are used to move the medication from the first stage 305 to the second stage 310 and from the second stage 310 to the pill delivery and lock-out module.

Figure 4:
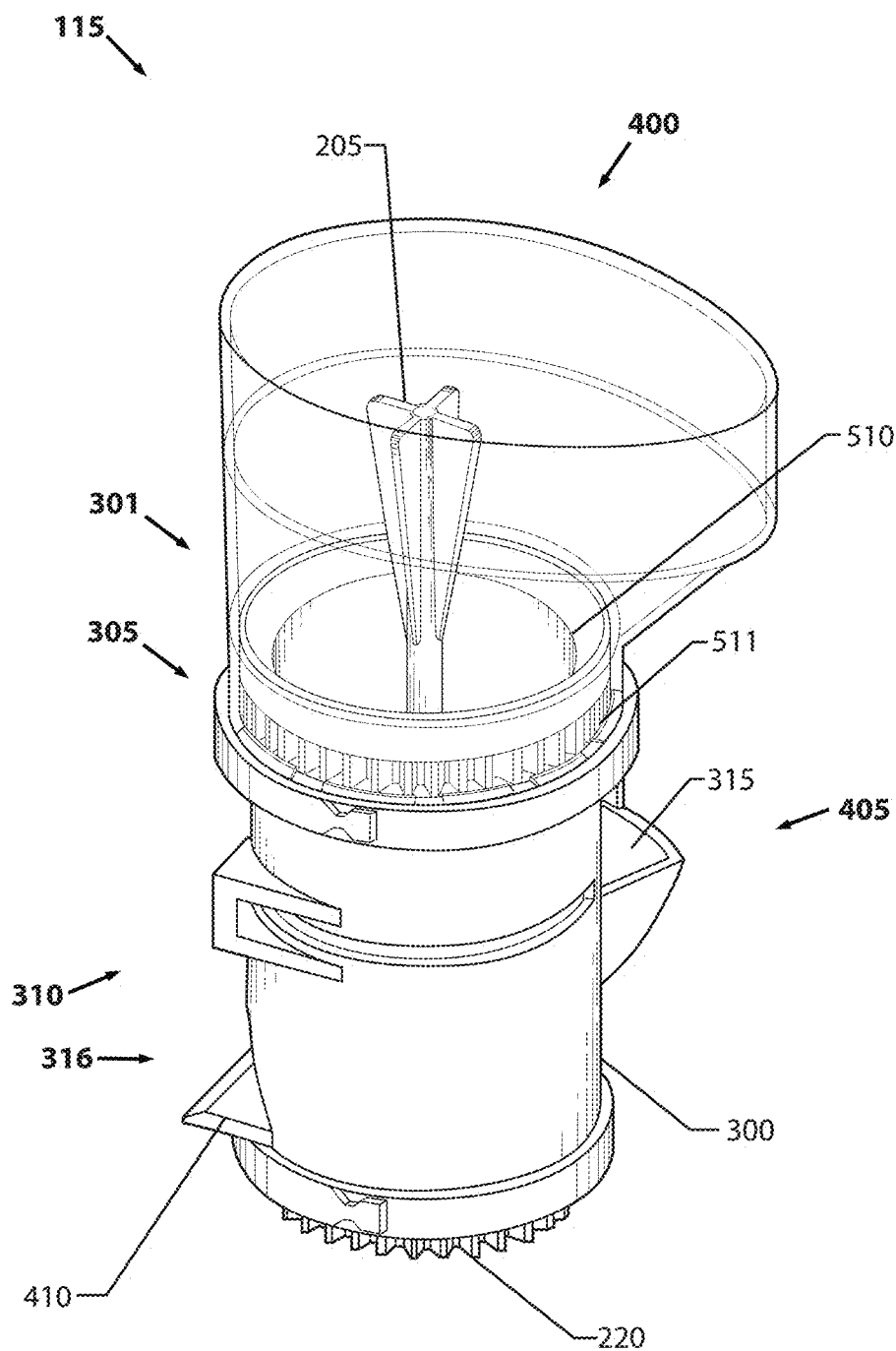
FIG. 4 is an illustration of a perspective view of one embodiment of a reservoir that is contained within the automated medication adherence system.

FIG. 4 is an illustration of a perspective view of one embodiment of a reservoir that is contained within the automated medication adherence system. FIG. 4 shows that each reservoir 115 within the automated medication adherence system may comprise a hopper 301 and a generally cylindrical outer wall 300. The hopper 301 may comprise or be connected to a top portion 400 of the reservoir 115. The top portion 400 may be covered by a rotating reservoir cover assembly 1105 that simultaneously opens and closes all reservoirs 115, allowing access from the pill loading assembly to the reservoir 115 when the rotating reservoir cover assembly 401 is open and preventing contamination and allowing transportation when the rotating reservoir cover assembly 1105 is closed. Additionally, the outer wall 300 may comprise or otherwise be connected to one or more chutes 405, 410. The first stage 305 of the reservoir 115 may comprise a first chute 405 to help guide medication traveling from the first stage 305 to the second stage 310. The first chute 405 may be an extension of the first opening 315. Likewise, the second stage 310 of the reservoir 115 may comprise a second chute 410 to help guide medication being dispensed into a pill delivery and lock-out module. The second chute 410 may be an extension of the second opening 316.

FIG. 4 also shows show the inner wall 510 may be comprised of gear teeth 511 and how the inner wall 510 may be substantially contained within the outer wall 300, such that the inner wall 510 may be turned, via gear teeth 511, within the outer wall 300. As shown, the gear teeth 511 may be preferably accessible through the outer wall 300. FIG. 4 also shows how the gear teeth 220 may be accessible through the outer wall 300.

FIG. 4 also shows how the hopper 301 may be designed to contain and be filled with medication, which may be prevented from clumping by the rotation of the fin portion 205.

Figure 5:
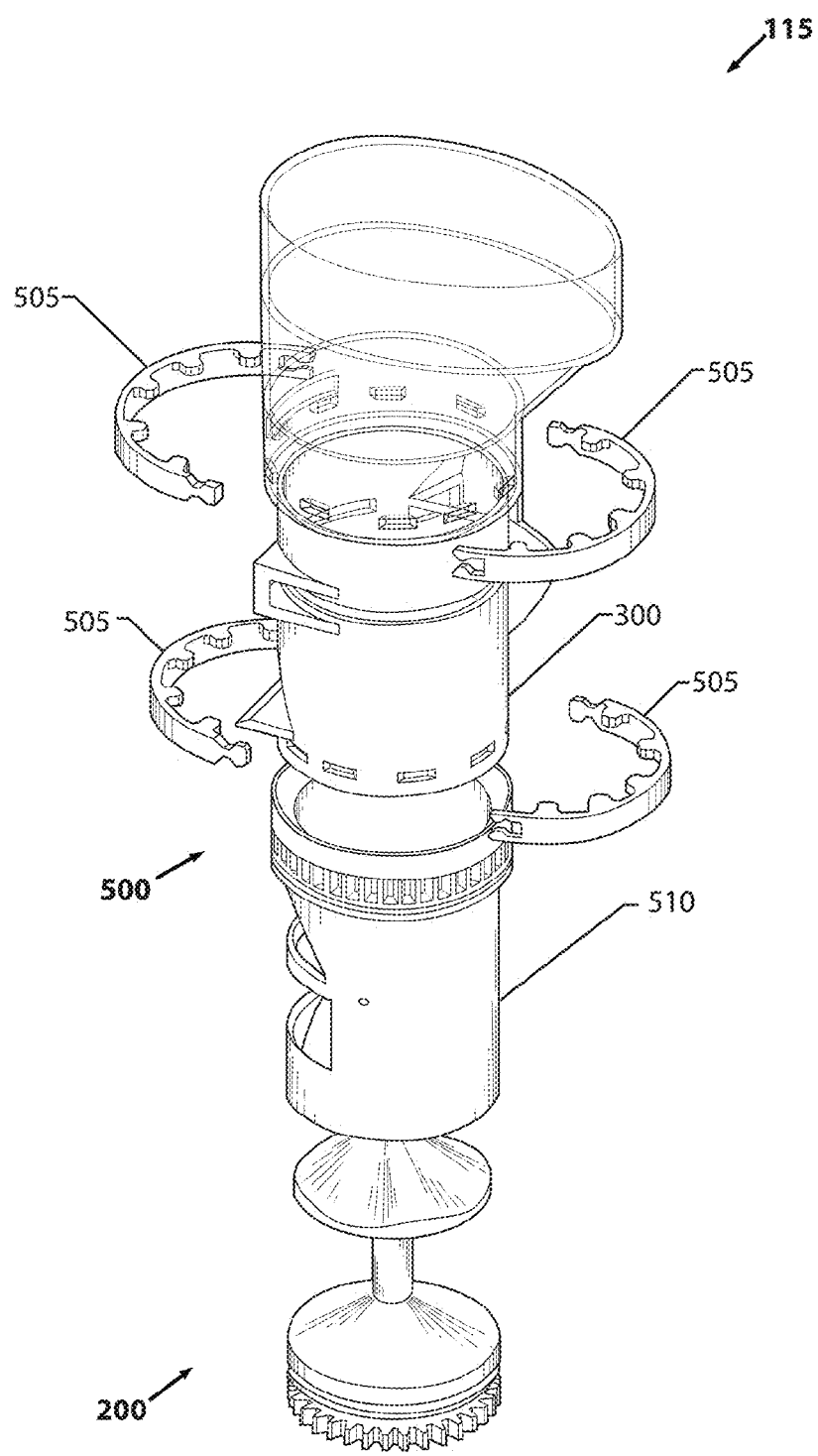
FIG. 5 is an illustration of an exploded view of one embodiment of a reservoir that is contained within the automated medication adherence system.

FIG. 5 is an illustration of an exploded view of one embodiment of a reservoir that is contained within the automated medication adherence system. FIG. 5 shows that each reservoir 115 within the automated medication adherence system may comprise a multi-component receptacle. FIG. 5 shows that the reservoir 115 may comprise a central agitation stalk 200, walls 300, 510, and one or more retaining rings 505. The central agitation stalk 200 may generally provide a rotational and agitation motion such that each reservoir 115 may receive, store, and dispense medication in an extremely precise and accurate manner. The outer wall 300 and the inner wall 510 may rotate relative to each other, which in turn, may create different sizes of openings around the periphery such that medication may pass between from the first stage to the second stage or be dispensed into the pill delivery and lock-out module. The retaining rings 505 may provide support to the top and bottom portions of the outer wall 300 and assist the outer wall in containing inner wall 510. The rings 505 may also hold the stalk vertically in place within the inner wall 510, as shown in FIG. 6.

Figure 6:
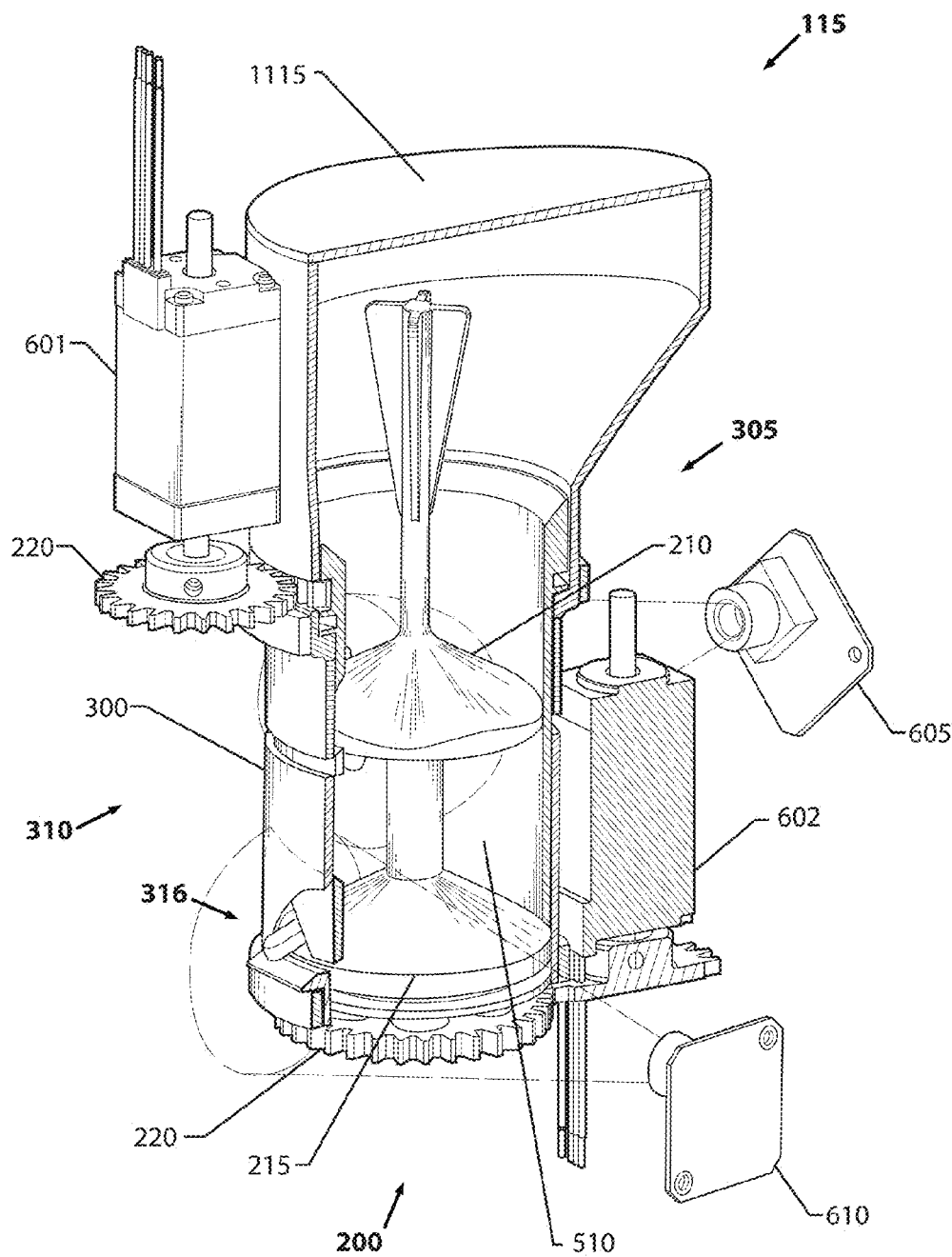
FIG. 6 is an illustration of a cross-section view of one embodiment of the interior of the automated medication adherence system and shows the sensors and actuators.

FIG. 6 is an illustration of a cross-section view of one embodiment of the interior of the automated medication adherence system. FIG. 6 shows that the automated medication adherence system may comprise one or more sensors 605, 610 and one or more actuators 601, 602. The sensor 605 may be configured to sense when a single pill, or a specific dosage of pills moves from the first stage 305 to the second stage 310. The sensor 605 may be an optical sensor, preferably a camera sensor, but other types of sensors may be used. The sensor 605 may preferably be positioned to monitor movement and ejection of a pill through the first opening 315. The sensor 610 may be configured to sense when a single pill, or a specific dosage of pills moves from the second stage 310 to the pill delivery and lock-out module. The sensor 610 may be an optical sensor, preferably a camera sensor, but other types of sensors may be used. The sensor 610 may preferably be positioned to monitor movement and ejection of a pill through the second opening 316.

The sensors 605, 610 are preferably connected to the computing component of electronic interface, such that the automated medication adherence system can detect when a pill has transferred to the second stage 310 or to the pill delivery and lock-out module.

FIG. 6 also shows how the actuators 601 and 602 interconnect with the inner wall 510 and the central agitation stalk 200, respectively, through the gear teeth 511 and 220, respectively. The actuators 601, 602 are controlled by the computing component of the electronic interface, such that the automated medication adherence system may accurately and precisely dispense medication of almost any size or shape. The actuator 601, as shown, may cause the inner wall 510 to rotate, such that the first and/or second opening 316 may be created and/or closed as needed to move the medication and control the ejection through the automated medication adherence system. The outer wall 300 and the inner wall 510 each may have openings that, when aligned by the rotation of the inner wall 510, create openings 316. The actuator 601 may also provide agitation, which may declump the medication, in the event that a sensor 605, 610 detects such clumping, and/or that may cause the medication to eject through the openings 315, 316 in a controlled manner.

The actuator 601, as shown, may cause the wave surface 210 to rotate, such that the medication resting on the wave surface 210 is brought to the first opening. Though agitation and rotation of actuators 601 and/or 602, the pill on the wave surface 210 may be caused to go through the first opening and down to the second stage 310, ideally one pill at a time. The sensor 605 may then inform the computing component that a single pill has successfully been moved and the actuator 601 may then close the first opening by reversing (or continuing) the rotation of the inner wall 510. Similarly, the actuator 602, as shown, may cause the ribbed cone surface 215 to rotate, such that the medication resting on the ribbed cone surface 215 may be brought to the second opening 316. Though agitation and rotation of the actuators 602 and/or 601, only one pill on the ribbed cone surface 215 may be caused to go through the second opening 316 and out to the pill delivery and lock-out module. The sensor 610 may then inform the computing component that the single pill has successfully been moved and the actuator 602 may then close the second opening 316 by reversing (or continuing) the rotation of the inner wall 510. This process may be repeated until the correct dosage has been delivered from to the pill delivery and lock-out module.

Figure 7:
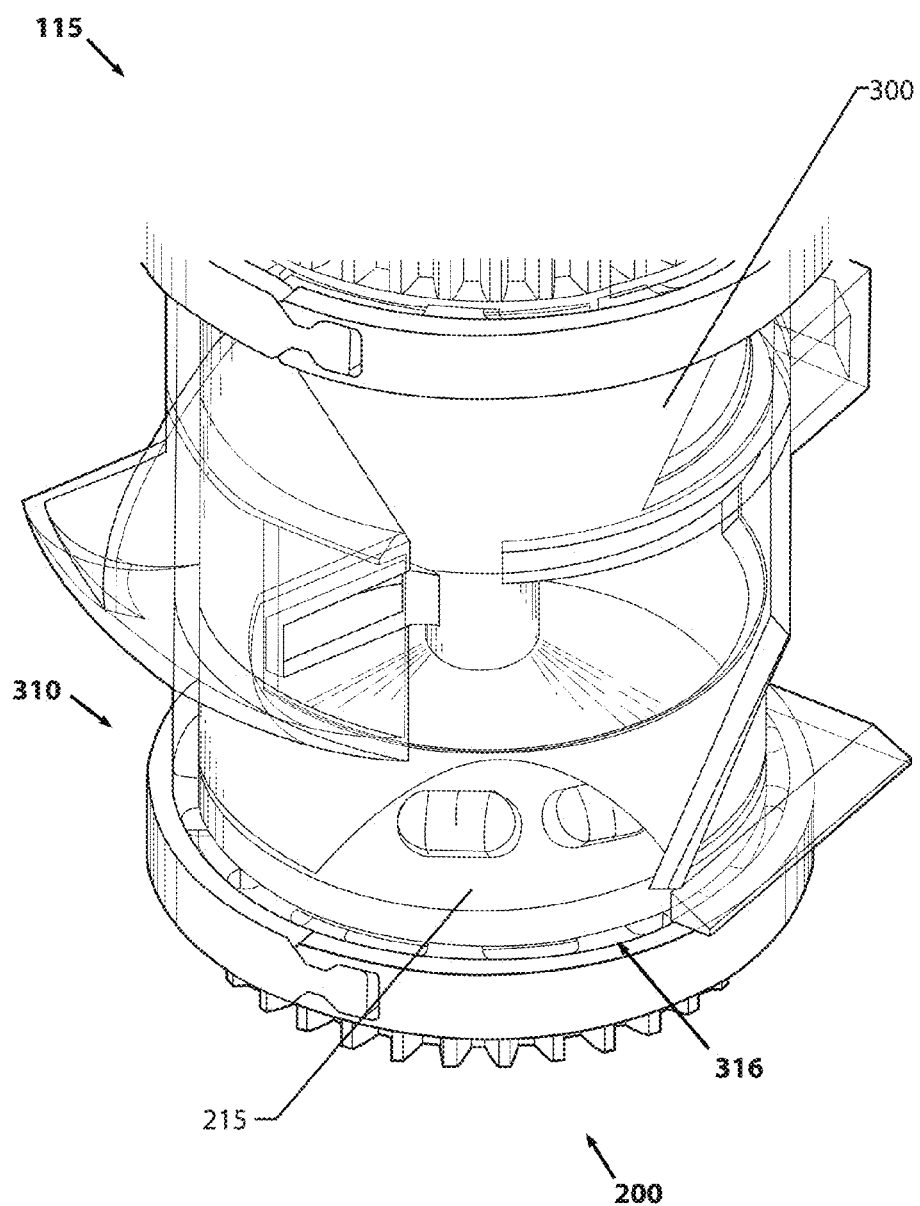
FIG. 7 is an illustration of a close-up view of one embodiment of the second stage of a reservoir that is contained within the automated medication adherence system.

FIG. 7 is an illustration of a close-up view of one embodiment of the second stage of a reservoir that is contained within the automated medication adherence system. FIG. 7 shows that the second stage 310 of a reservoir 115 may house medication on the ribbed cone surface 215 of the central agitation stalk 200 prior to dispensing the medication into the pill delivery and lock-out module. Preferably, the amount of medication on the ribbed cone surface 215 is only a small number of pills, and may be a single dosage of the medication to be delivered to the pill delivery and lock-out module. The actuator may align the outer wall 300 and the inner wall of the reservoir 115 such that the opening 316 (shown in FIG. 8) is not yet formed. Thus, the medication in the second stage 310 cannot yet exit. The ribbed cone surface 215 may be agitated by the actuator at specific amplitudes and frequencies in order to facilitate the separation of the medication on the ribbed cone surface 215, in order to line up one pill behind the other so that the medication can be transferred, one pill at a time, to the pill delivery and lock-out module. The actuator may continue (or reverse) the rotation of the ribbed cone surface 215 until each pill conforms to its exit position, preferably lengthwise. Additionally, using pre-programmed medication data and algorithms, the rotation and agitation parameters may adjust the opening 316 to best match the dimensions of the pill.

Figure 8:
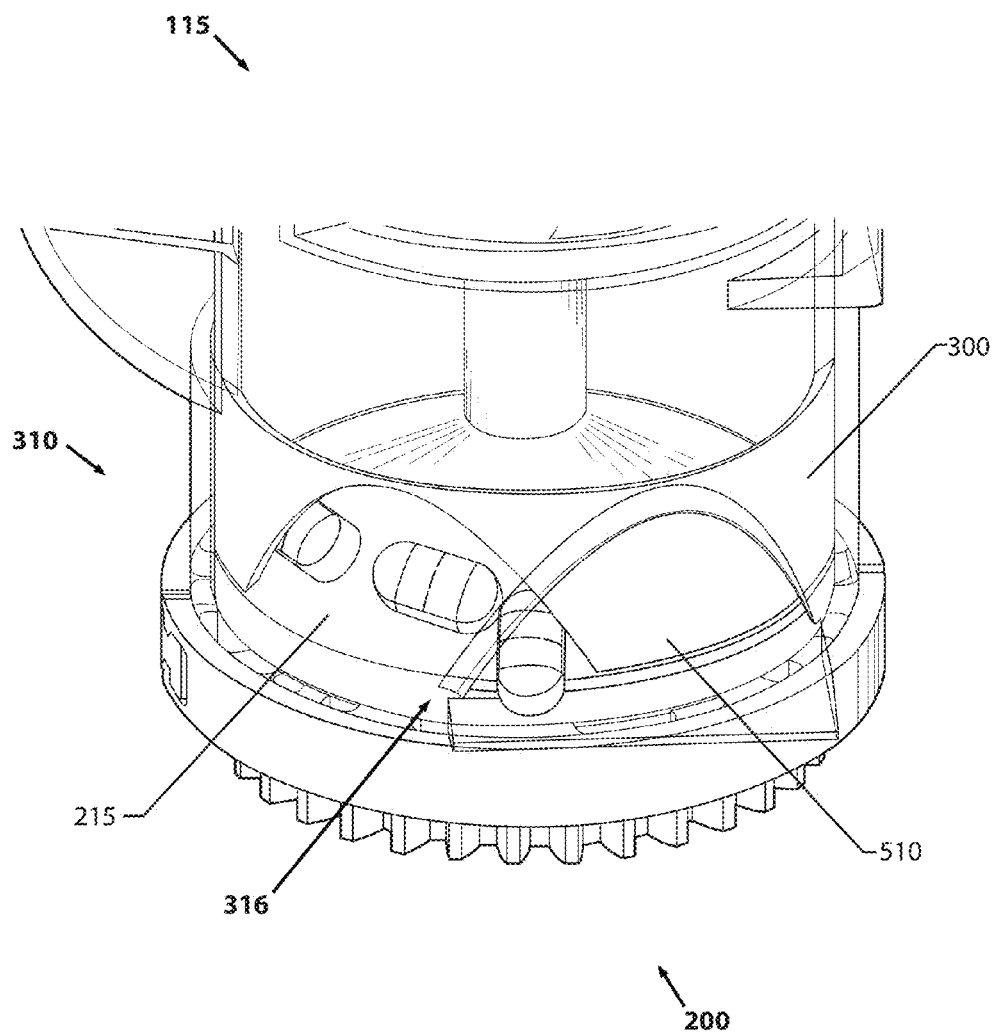
FIG. 8 is an illustration of a close-up view of one embodiment of a reservoir that is contained within the automated medication adherence system with continuously variable openings to best match the solid geometry of the pill loaded into a specific reservoir.

FIG. 8 is an illustration of a close-up view of one embodiment of a reservoir that is contained within the automated medication adherence system with continuously variable openings to best match the solid geometry of the pill loaded into a specific reservoir. FIG. 8 shows that the second stage 310 of a reservoir 115 may house medication on the ribbed cone surface 215 of the central agitation stalk 200 prior to dispensing the medication into a pill delivery and lock-out module. The outer wall 300 and the inner wall 510 of the reservoir 115 may be aligned such that the second opening 316 around the periphery is formed and accessible for medication dispensing at a desired period of time. When the medication reaches the second opening 316 around the periphery, the medication, through gravity, may pass through the second opening 316. Agitation may be provided by the central agitation stalk 200 in order to assist the medication in passing through the second opening 316. Algorithms for agitation and rotation parameters may be pre-programmed into the electronic interface and may include specific amplitudes and frequencies in order to facilitate the travel of the medication through the automated medication adherence system. The automated medication adherence system may accommodate medication generally ranging from about 3 to about 28 millimeters, but the reservoir size, openings, and agitation and rotation parameters may be changed to increase the range of pill sizes and solid geometries. Once the dosage of medication has been dispensed, the electronic interface may close the second opening 316 and provide an alert that the medication is available for consumption.

Figure 9:
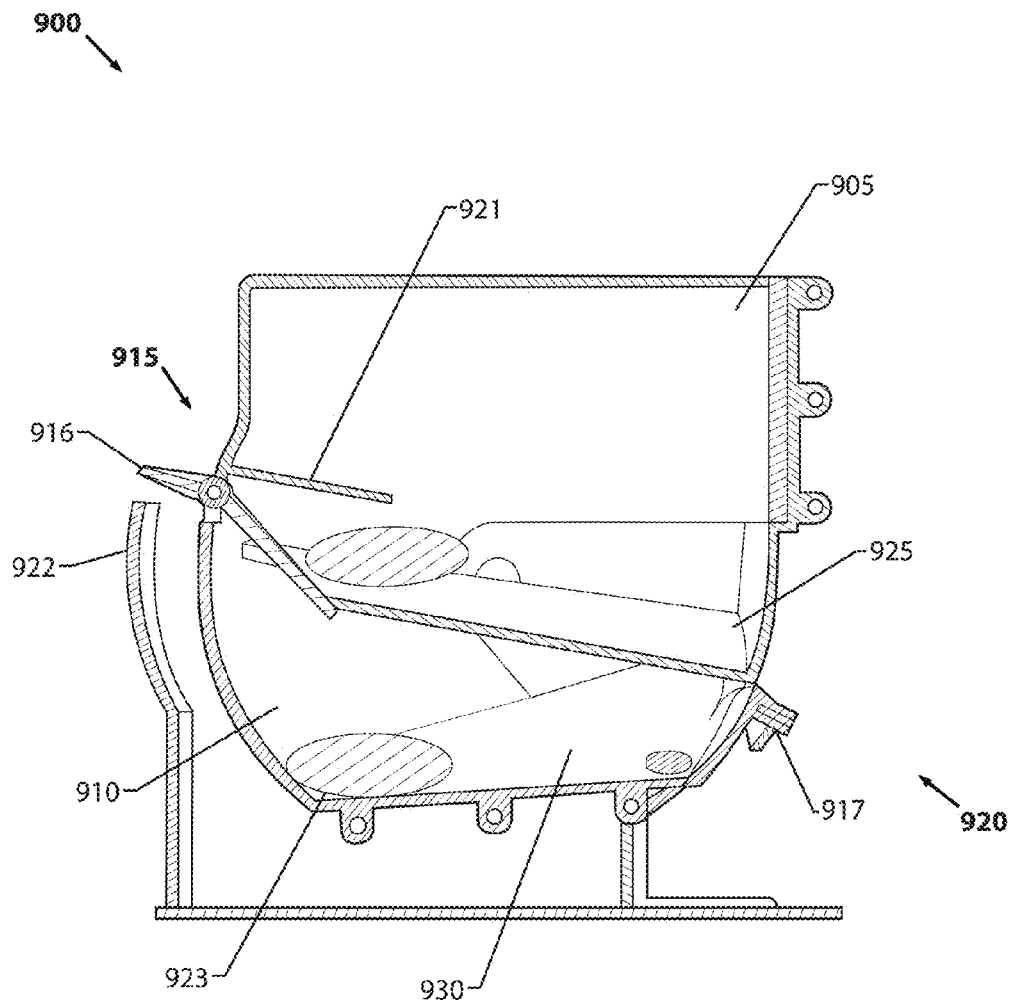
FIG. 9 is an illustration of another embodiment of a reservoir that is contained within the automated medication adherence system.

FIG. 9 is an illustration of another embodiment of a reservoir that is contained within the automated medication adherence system. FIG. 9 shows that the reservoir 900 may comprise two successive stages, a first stage 905 and a second stage 910. The two successive stages may be configured to be stacked, such that the first stage 905 is substantially above the second stage 910. A user may load medication into the first stage 905 of the reservoir 900. A plurality of pills may move from the first stage 905 to the second stage 910 through a first opening 915. Sensors, rotational and agitation actuators, and logic algorithms may ensure that only a specified number of pills, usually one or two pills, are transferred—preferably one pill at a time—from the first stage 905 to the second stage 910. The second stage 910 may comprise a second opening 920 for allowing the medication to be dispensed, preferably one pill at a time, to a pill delivery and lock-out module. A baffle 921 may be positioned over the first opening 915 to prevent pills from going directly from the first stage 905 to the second stage 910 and to reduce the static pressure thereby facilitating a gradual transition of pills from the first stage 905 to the second stage 910. FIG. 9 also shows that the openings 915, 920 may comprise or be connected to chutes 925 and 930 and spring-loaded gates 916 and 917. The reservoir 900 may rotate to agitate the pills and to transfer the pills from the first stage 905 to the second stage 910 and counter-rotate to transfer the pills from the second stage 910 to the pill delivery and lock-out module. During rotation of the reservoir 900, the fixed gate opener 922 may help open the spring-loaded gate 916 in order to transfer pills from the first stage 905 to the second stage 910. A pill detection area 923 may detect the number of pills that have transferred from the first stage 905 to the second stage 910. During counter-rotation of the reservoir 900, a second spring-loaded gate 917 may open in order to transfer pills from the second stage 910 to the pill delivery and lock-out module. As the pills pass through openings 915 or 920, the chutes 925, 930 may direct them to travel along a predetermined path.

Figure 10:
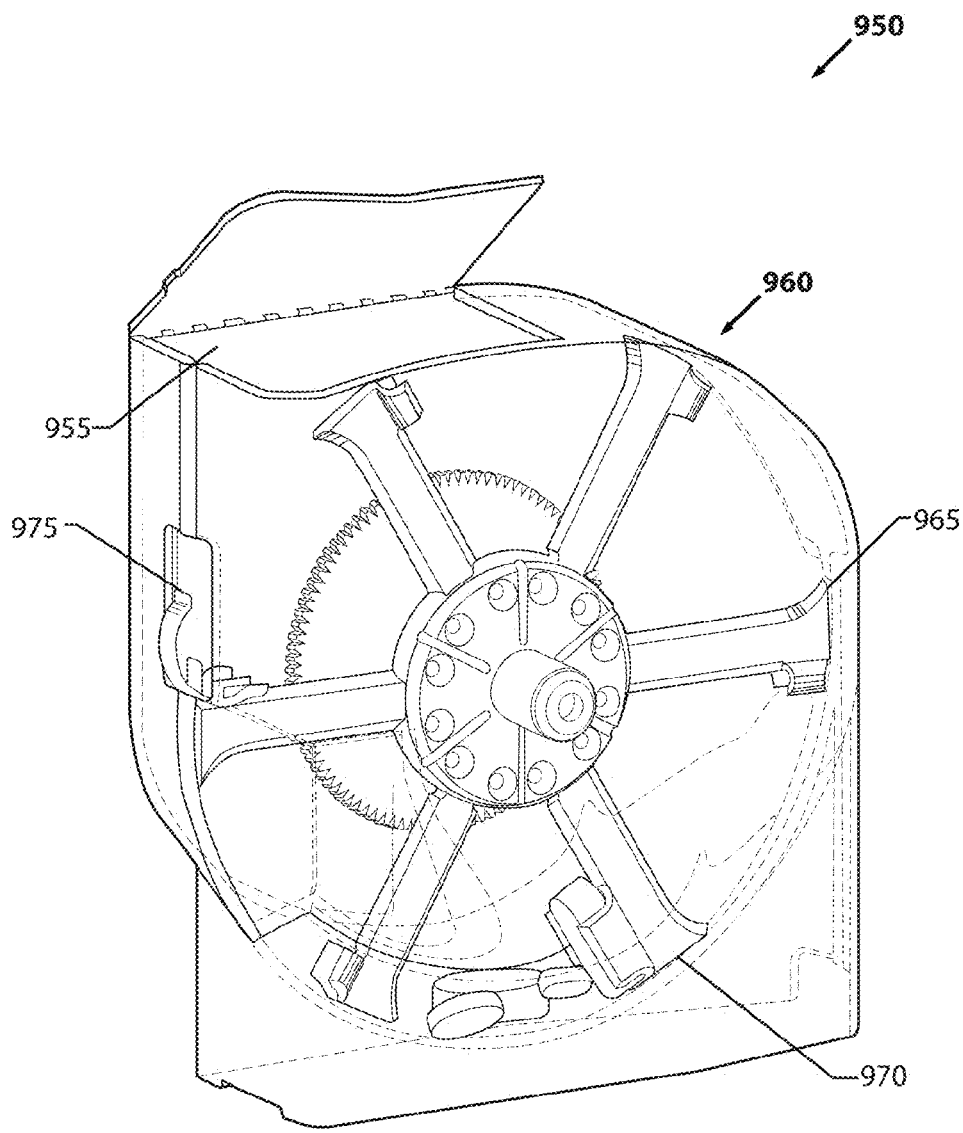
FIG. 10 is an illustration of another embodiment of a reservoir that is contained within the automated medication adherence system.

FIG. 10 is an illustration of another embodiment of a reservoir that is contained within the automated medication adherence system. FIG. 10 shows that once the reservoir 950 is aligned with the pill loading assembly in the access cover, a user may load medication into the reservoir cover assembly 955, allowing access from the pill loading assembly to the reservoir 950 when the reservoir cover assembly 955 is open and preventing contamination and allowing transportation when the reservoir cover assembly 955 is closed. Typically, gravity may be used to assist in loading medication through the reservoir cover assembly 955 into the reservoir 950. The reservoir 950 may preferably house a heterogeneous type of medication, where medication may be one of many different sizes or shapes. As shown in FIG. 10, the reservoir 950 may comprise a wheel 960. The wheel 960 may preferably comprise six (6) pill scoops 965. The end 970 of each pill scoop 965 may comprise a different geometry to conform to different pill sizes or shapes. When a pill is ready for dispensing, proprietary controlled vibration, motion, and shaking of the wheel 960 may assist the pill scoop 965 in retrieving a single pill from the plurality of pills housed in the reservoir 950. Matching the pill scoop 965 with the appropriate pill size and shape may be determined by a vision or sensor system or information stored in the pharmaceutical and/or proprietary databases. Preferably, the wheel 960 may rotate in either direction, to align the pill scoop 965 into position. Then the wheel 960 may rotate in a clockwise direction to sweep through the plurality of pills and scoop up the appropriate pill. The vision or sensor system may determine if the pill scoop 965 has (i) a single and correct pill ready for ejection, (ii) has more than one pill, or (iii) is empty. Preferably, only a single pill will be located on the end 970 of the correct arm of pill scoop 965. If more than one pill is on the pill scoop 965, the wheel 960 may shake or agitate to knock off excess pills. If the pill scoop 965 is empty, the pill scoop 965 may try to scoop up the correct pill again. The pill may exit the reservoir 950 via a spring-loaded gate 975. When the pill is ready for ejection, the wheel 960 may rotate in the counter clockwise direction slightly to allow the ejection arm (not shown) to enter to reservoir 950. Once the ejection arm has entered the reservoir 950 via the spring-loaded gate 975, the wheel 960 may rotate in the clockwise direction to bring the pill into position with the ejection arm. The ejection arm may then retract to eject a pill.

Figure 11A:
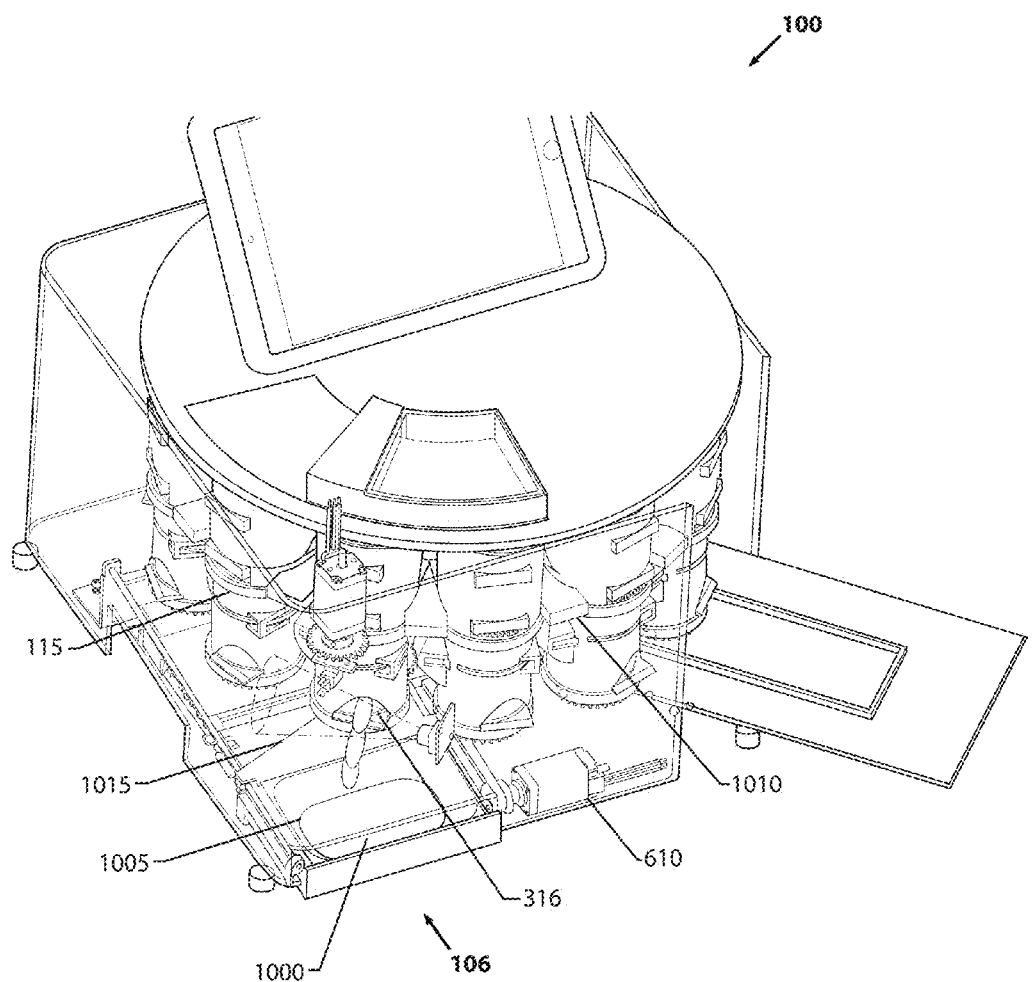
FIG. 11A is an illustration of a close-up view of one embodiment of the pill delivery and lock-out module in its neutral position that is contained within the automated medication adherence system.

FIG. 11A is an illustration of a close-up view of one embodiment of the pill delivery and lock-out module in its neutral (holding pill delivery and lock-out module) position that is contained within the automated medication adherence system. FIG. 11A shows that the reservoirs 115 are preferably configured to isolate a dosage of medication contained in the specific reservoir 115 and then deliver the dosage to the pill delivery and lock-out module 106. The pill delivery and lock-out module 106 may comprise a dispensing tray 1000, a transporter 1005, and a lock-out tray, which is created by the axial movement of the transporter 1005 in relation to the other components described below. The pill delivery and lock-out module 106 may be substantially housed within the interior of the automated medication adherence system 100 when holding medication. Preferably, the rotating carrier 1010 rotates, such that the appropriate reservoir 115 may be next to the pill delivery and lock-out module 106. Then an actuator may cause the reservoir 115 to rotate, such that the medication resting on the ribbed cone surface may brought to the second opening 316. Through agitation and rotation of the actuators, the medication on the ribbed cone surface may be caused to go through the second opening 316 and out to the pill delivery and lock-out module 106. The dosage of medication may be one or more pills. The dosage may come from one or more reservoirs 115. Once the entire dosage is within the dispensing tray 1000, the user may then be signaled to collect the dosage. A sensor 610 may inform the computing component that the medication has successfully been moved and the actuator may close the second opening 316 by rotation of the inner wall of the reservoir 115. This process may be repeated until the correct dosage of medication(s) has been delivered to the pill delivery and lock-out module 106. The sensor 610 may preferably be positioned to monitor movement of medication through the second opening 316 to the pill delivery and lock-out module 106. The sensor 610 may take pictures and store data confirming that a dosage and/or total dosage of medication was dispensed. When the prescribed dose of medication for that dosage time period has been delivered to the pill delivery and lock-out module 106, the pill delivery and lock-out module 106 may move to the exterior of the automated medication adherence system 100 to a forward position so a user may then take the dosage of medication from the pill delivery and lock-out module 106. Additionally, notification may alert a user the medication is ready for consumption.

FIG. 11A also shows that if one or more pills were erroneously dispensed, the pill delivery and lock-out module 106 may remain in the neutral position, below the reservoir 115, and hold the pills that were dispensed from the second opening 316. The transporter 1005 may also move in reverse to transfer any erroneously dispensed pills to a lock-out tray 1015 (shown in FIG. 11C). Preferably, when the lock-out tray 1015 operates, a notification may be sent to the user, any authorized individual, and/or a health care provider. In this manner, missed or incorrect dosages may be dealt with appropriately.

Figure 11B:
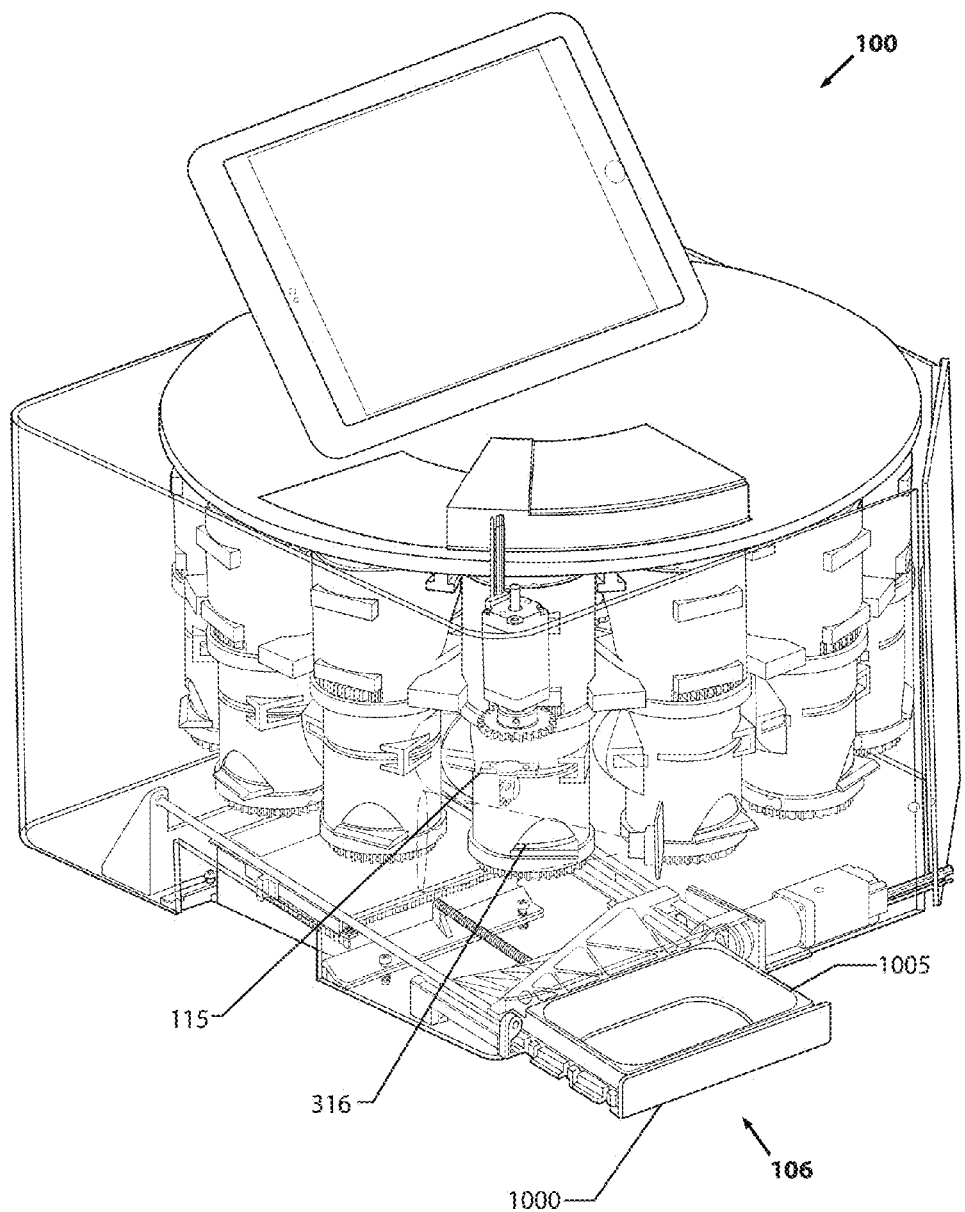
FIG. 11B is an illustration of a close-up view of one embodiment of the pill delivery and lock-out module in its forward position that is contained within the automated medication adherence system.

FIG. 11B is an illustration of a close-up view of one embodiment of the pill delivery and lock-out module in a forward position. FIG. 11B shows when one or more pills are dispensed from the second opening 316 of a reservoir 115, the transporter 1005 may move forward to eject the dispensing tray 1000 into a forward position when the patient is ready to take the pills. If the pill delivery and lock-out module 106 is in the forward position and the pills are not removed by the patient after a period of time, the transporter 1005 may also move in reverse to transfer the pills to a lock-out tray 1015. A dosage of medication may rest within the pill delivery and lock-out module 106 until the medication is ready to be collected by a user.

Figure 11C:
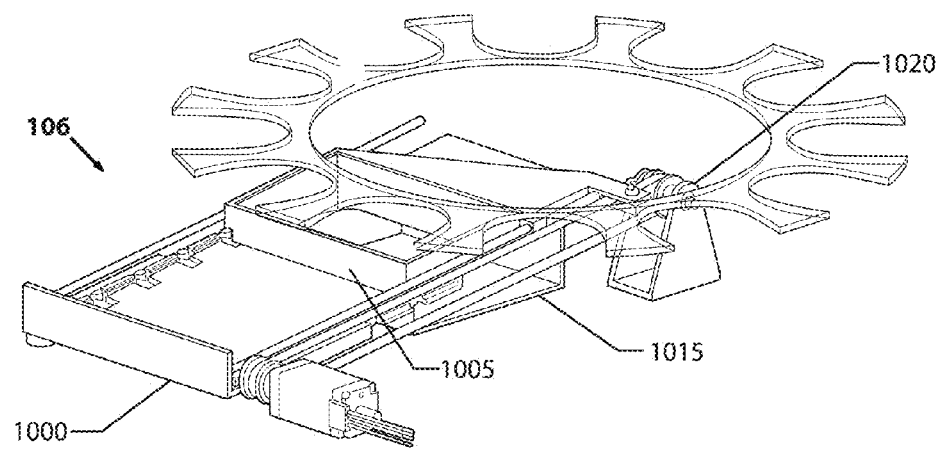
FIG. 11C is an illustration of one embodiment of the pill delivery and lock-out module in its reverse (lock-out tray) position that is contained within the automated medication adherence system.

FIG. 11C is an illustration of one embodiment of the pill delivery and lock-out module in its reverse (lock-out tray) position that is contained within the automated medication adherence system. FIG. 11C shows that if a dosage of medication is not retrieved after a pre-determined period of time or if the dosage of medication has been dispensed incorrectly, the transporter 1005 may move or slide backward and guide the medication from the dispensing tray 1000 of the pill delivery and lock-out module 106 to a lock-out tray 1015. Once the medication is stored in the lock-out tray 1015, a user adherence record may be updated and the transporter 1005 may move back into its neutral position. In this manner, the next dosage may not get mixed up with the previous dosage, avoiding an over dosage, and an incorrect dosage may be held in the lock-out tray 1015. Preferably, when the lock-out tray 1015 operates, a notification may be sent to the user, one or more authorized individuals, and/or one or more health care providers. In this manner, missed or incorrect dosages may be dealt with safely and appropriately and double or wrong dosage is prevented. FIG. 11C shows that actuator 1020 may be used to slide the transporter 1005 back and forth to dispense or retrieve an unused or incorrect dosage.

Figure 12:
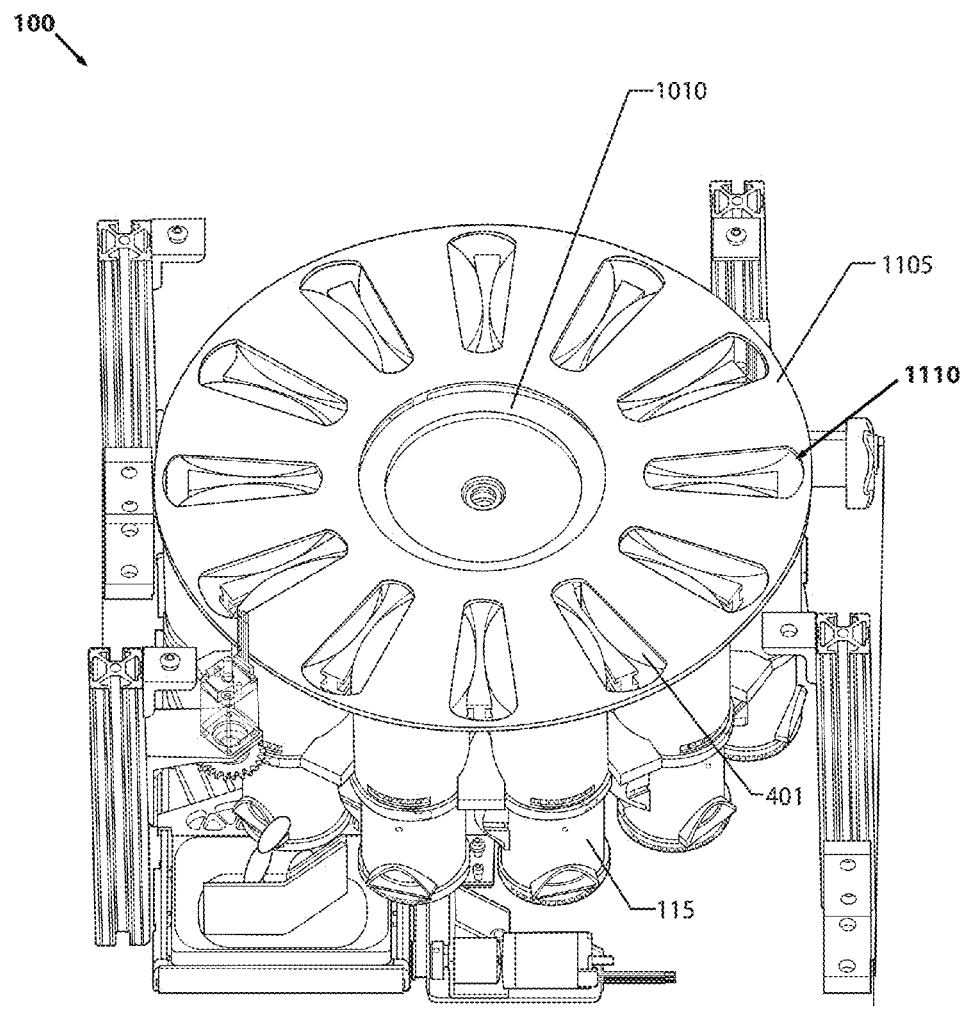
FIG. 12 is an illustration of one embodiment of the reservoir cover mechanism that opens and closes a reservoir fill opening that is contained within the automated medication adherence system.

FIG. 12 is an illustration of one embodiment of the reservoir cover mechanism that opens and closes a reservoir fill opening that is contained within the automated medication adherence system. FIG. 12 shows the automated medication adherence system 100 may comprise an access cover. The access cover may be movable to an open or closed position. When the access cover is in a closed lockable position, a pill loading assembly located on at least one portion of the top access cover may provide access between the exterior of the housing and the interior of the housing in order to load medication into the reservoirs 115. A rotating carrier 1010, may hold the reservoirs 115 in position wherein the electronic interface may actuate a motor to rotate the rotating carrier 1010 in order to align a pre-determined reservoir 115 with the pill loading assembly of the access cover, such that medication may travel through the pill loading assembly and into the correct, known, and identified reservoir 115. The rotating carrier 1010 may then rotate again to allow a user to load additional medications into different reservoirs 115. The interior of the housing may also comprise a rotary lid 1105. The rotary lid 1105 may be positioned above the reservoirs 115 and may passively rotate in response to the clockwise or counter clockwise rotation of the rotating carrier 1010. The rotary lid 1105 may provide access to the interior of the reservoirs 115 when the openings 1110 in the rotary lid 1105 align with the openings of the rotating reservoir cover assembly 401. Likewise, the rotary lid 1105 may prevent access to the interior of the reservoirs 115 when the openings 1110 in the rotary lid 1105 do not align with the openings of the rotating reservoir cover assembly 401. An additional fixed cover may be present above the rotary lid 1105.

Figure 13:
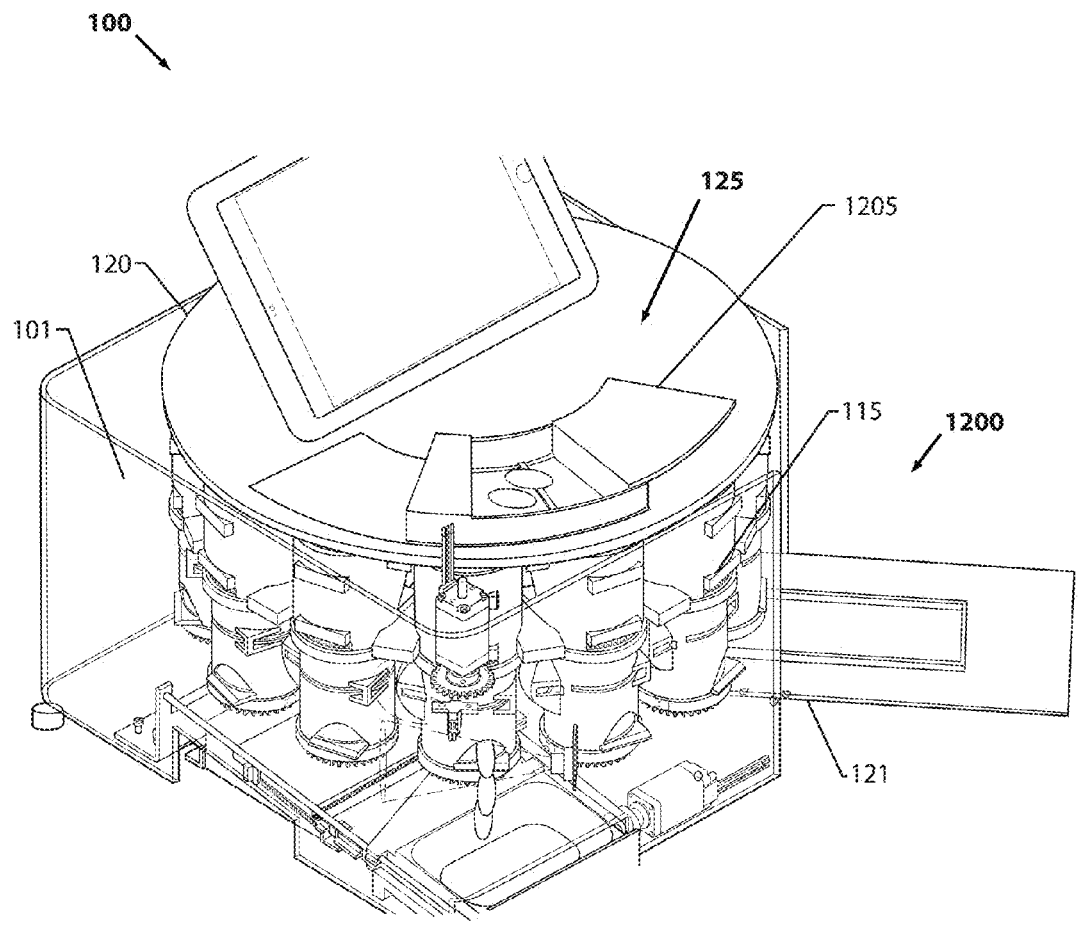
FIG. 13 is an illustration of one embodiment of the reservoir loading door and the pill loading assembly that are contained within the automated medication adherence system.

FIG. 13 is an illustration of one embodiment of the automated medication adherence system showing the reservoir loading door and the pill loading assembly. FIG. 13 shows the reservoir loading door 121 may be used to load or remove reservoirs 115 by the end user. The reservoir loading door 121 may be movable to an open position 1200 for manually placing or removing reservoirs 115 into the interior of the automated medication adherence system 100 or removing the reservoirs 115 one at a time. Preferably, the reservoir loading door 121 may slide individual reservoirs 115 in and/or out of the interior of the automated medication adherence system 100. When the reservoir loading door 121 is not in use, the reservoir loading door 121 may fold up in a vertical direction and form part of the exterior of the housing 101.

FIG. 13 also shows when the access cover 120 is in a closed lockable position, a pill loading assembly 125 located on at least one portion of the access cover 120 may provide access between the exterior of the housing 101 and the interior of the housing 101 in order to load medication into the reservoirs 115. Typically, gravity may be used to assist in loading medication through the pill loading assembly 125 into the reservoirs 115. The pill loading assembly 125 may also comprise a pill wiper 1205, which may wipe medication into the reservoirs 115. When the pill loading assembly 125 is not in use, the pill wiper 1205 may remain in a closed position, preventing access to the pill loading assembly 125.

Figure 14:
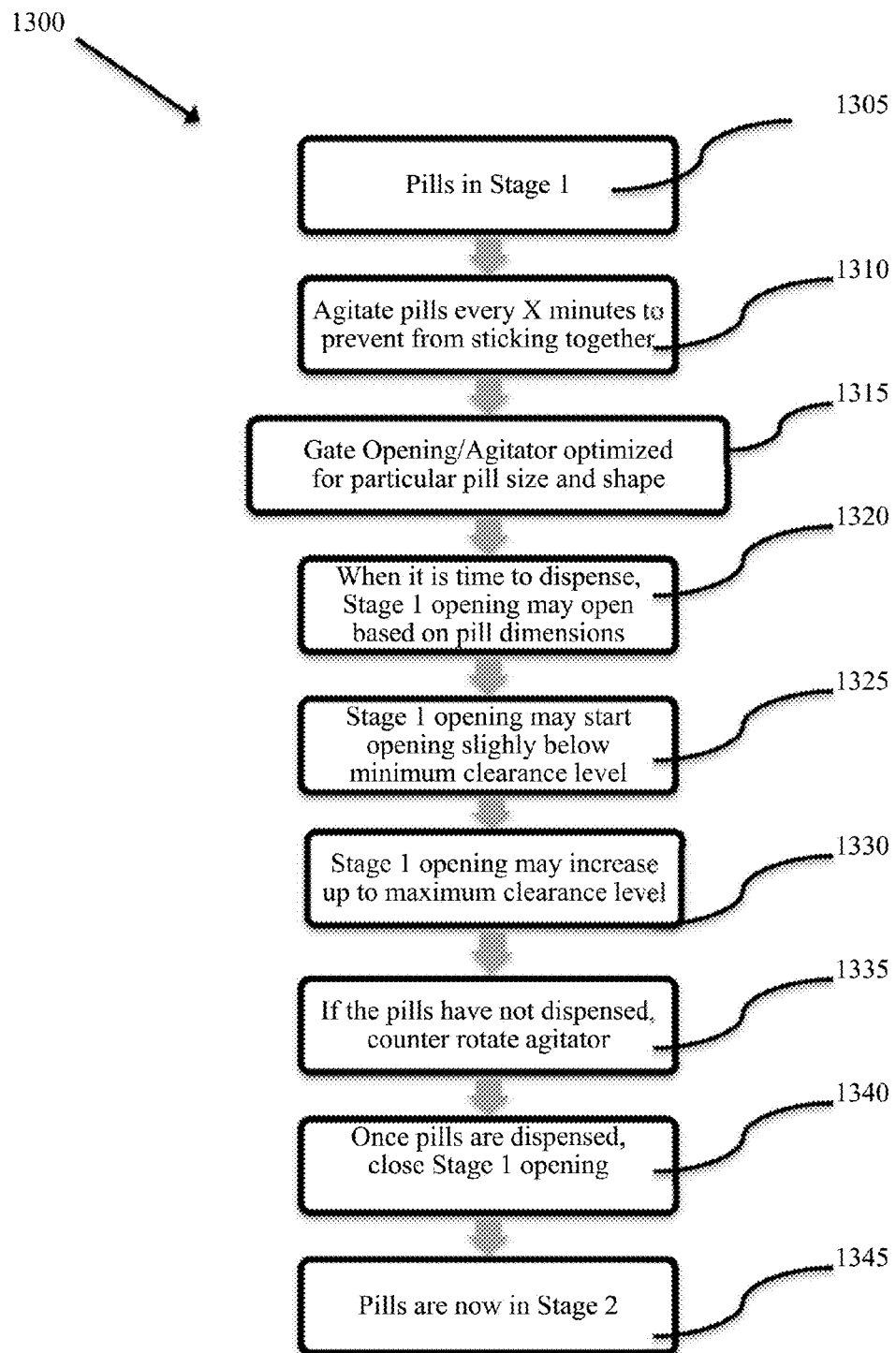
FIG. 14 is a flow block diagram of one embodiment of the method of medication moving through the first stage of the automated medication adherence system.

FIG. 14 is a flow block diagram of one embodiment of the method of medication moving through the first stage of the automated medication adherence system 1300. FIG. 14 shows that after a user loads medication into the automated medication adherence system, the medication may remain in the first stage 1305 of the reservoir for storage until the medication is ready to be transferred to the second stage. The agitator may agitate the reservoir using proprietary algorithms at set time intervals in order to prevent the medication from sticking to one another 1310. Similarly, the reservoir may agitate using calculated algorithms to begin transporting the medication toward the opening in the first stage using calculated rotation and counter rotation parameters. Preferably, the agitator may be optimized for a particular pill size and shape 1315. Accordingly, the opening in the first stage may start opening based on the medication's dimensions 1320. The opening may increase from a minimum clearance level 1325 until it has reached the maximum clearance level 1330. If the medication has not dispensed into the second stage, the agitator may counter rotate a number of full turns 1335. This may help the pills realign on the surface and may clear pill jams within the first stage. The sensor may detect when a single pill has been dispensed and immediately close the opening in the first stage. The medication should now be in stage two 1345.

Figure 15:
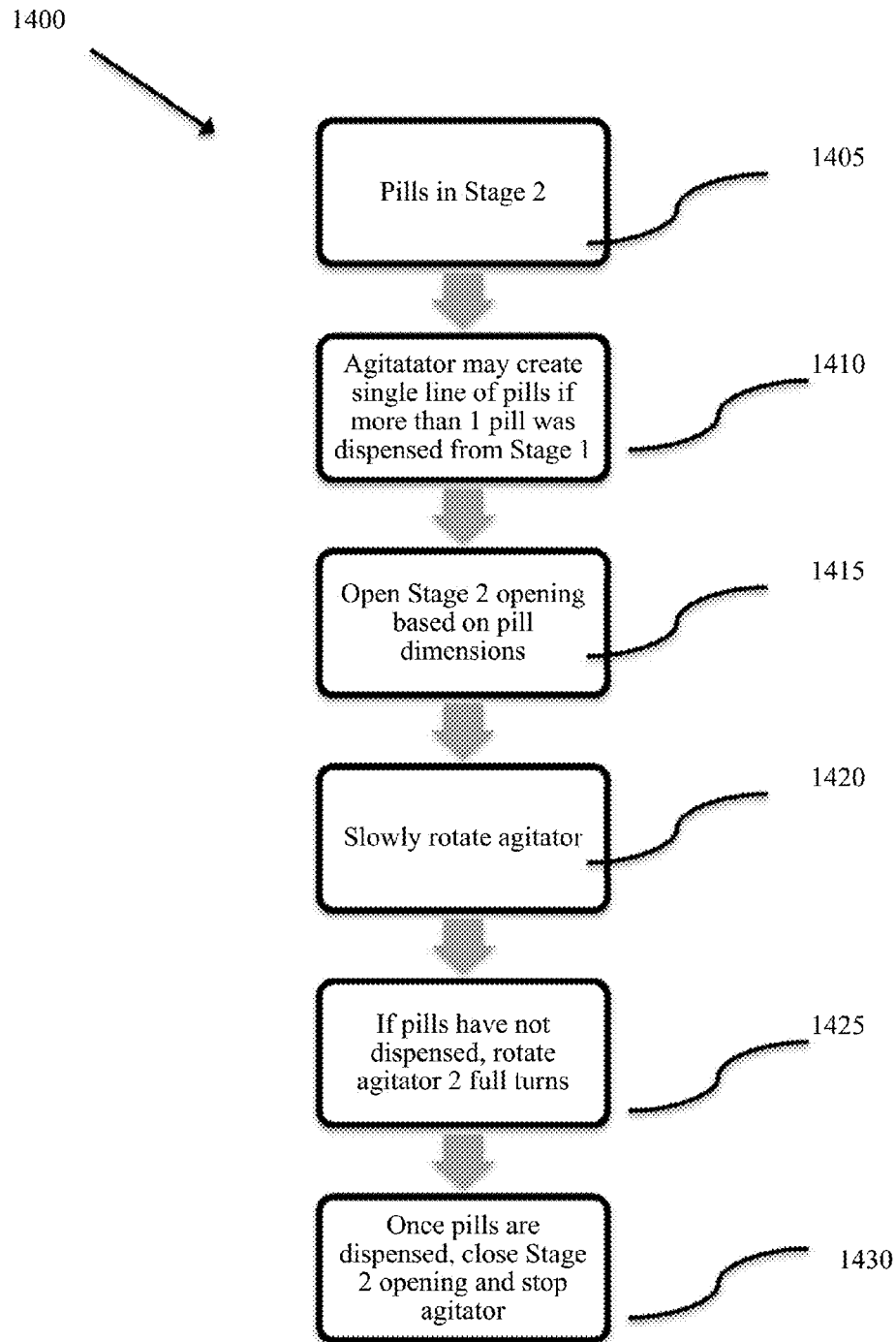
FIG. 15 is a flow block diagram of one embodiment of the method of medication moving through Stage 2 of the automated medication adherence system.

FIG. 15 is a flow block diagram of one embodiment of the method of medication moving through the second stage of the automated medication adherence system 1400. FIG. 15 shows that after that the medication may travel from the first stage to the second stage 1405. Once the medication is in the second stage, the agitator may rotate in order to line the medication up in single line along the surface of the second stage, if more than one pill was transferred from the first stage to the second stage 1410. The opening of the second stage may open based on the medication's dimensions 1415 and the agitator may slowly begin to rotate 1420 in order to help the medication dispense into the pill delivery and lock-out module. If the medication did not dispense, the agitator may rotate for two full turns 1425 in order to dispense the medication. A sensor may detect when a single pill has been dispensed into the pill delivery and lock-out module and the opening of the second stage may close and the agitator may stop rotating 1430. The pills may fall out via gravity from the second stage opening as the pills are rotated past the second stage opening.

Figure 16:
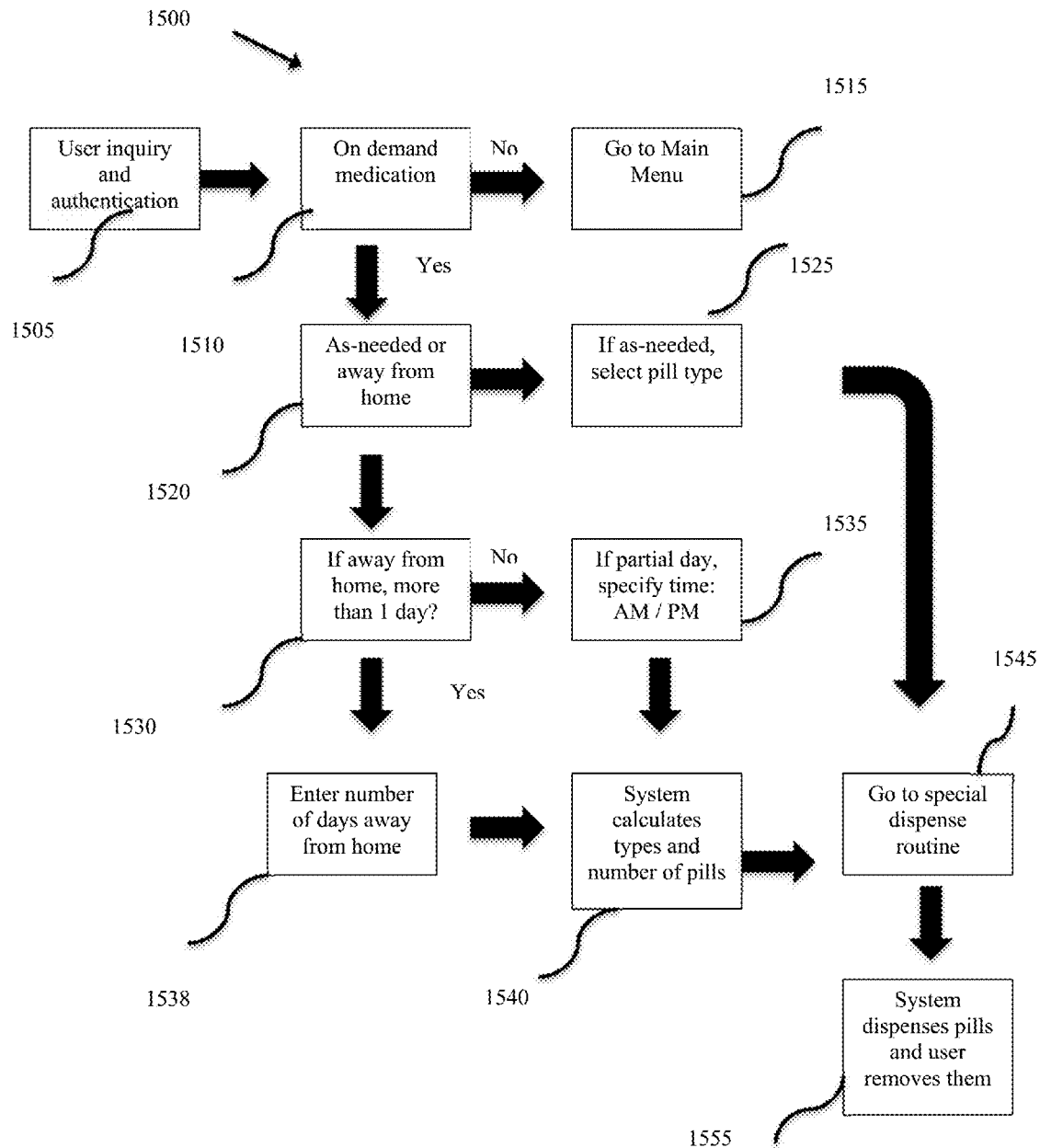
FIG. 16 is a flow block diagram of one embodiment of the method of taking medication on an as-needed or away from home basis.

FIG. 16 is a flow block diagram of one embodiment of the method of taking medication on an as-needed or away from home basis 1500. When a user engages with the automated medication adherence system, the automated medication adherence system may inquire as to the user's identity and authentication 1505. Although the automated medication adherence system does not require the user to do any programming, the user may be required to input, scan, or otherwise upload information relating to the user, the medication, the prescribing entity, and/or the prescription. If a user would like the use the automated medication adherence system for on demand medication 1510, the user may be directed to the Main Menu of the computing component 1515. Otherwise, the user may select a medication event such as an as-needed basis or away from home basis 1520. If the user decides to take the medication on an as-needed basis, the user may be prompted to select a pill type 1525. The medication may then undergo a special dispensing routine 1545. The automated medication adherence system may then dispense the medication and a user may remove the medication for consumption 1555. If the user has exceeded the maximum number of on-demand medications allowed over a pre-determined period of time, the system may not dispense anymore medication and may alert the user and a medical professional of this condition. If the user decides to take the medication on an away from home basis, the user may have to decide whether they will be away from home for more than one day 1530. If the user may be away from home for more than one day, the user may enter the number of days they will be away from home 1538. If the user will not be away from home for more than one day, the user may specify when they will be away, for example, in the morning and/or the evening 1535. The automated medication adherence system may then calculate the type and number of pills required by the user 1540. The medication may then undergo a special dispensing routine 1545. The automated medication adherence system may then dispense the medication and a user may remove the medication for consumption 1555.

Figure 17:
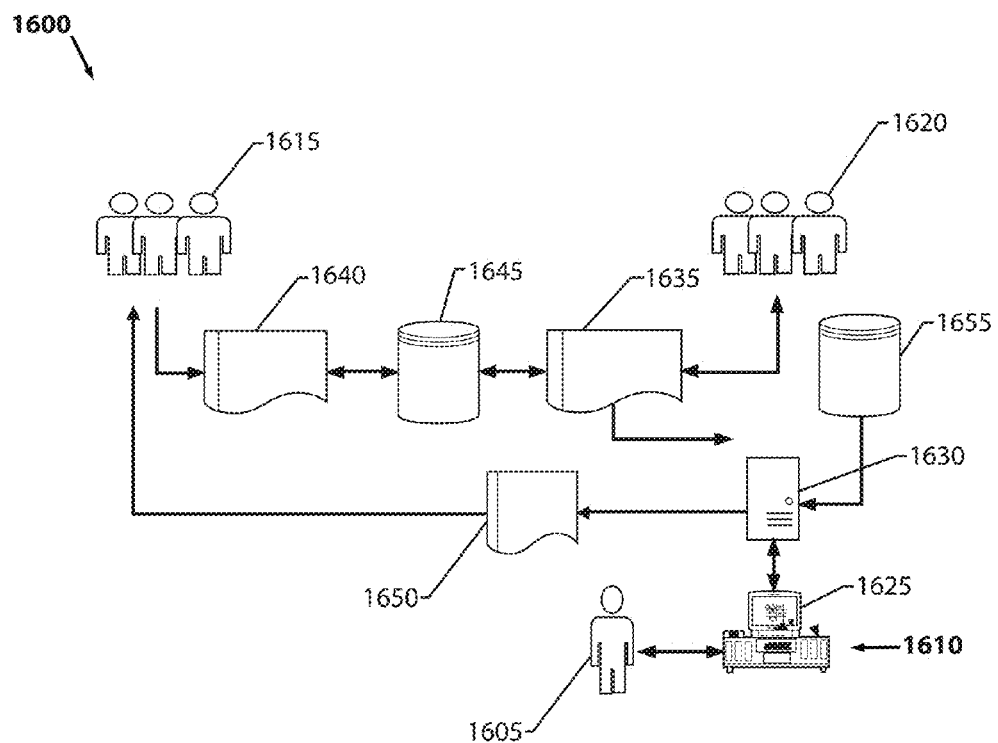
FIG. 17 is a flow block diagram of one embodiment of the method of programming the reservoirs and dispense logic using one or more algorithms using the computing component.

FIG. 17 is a flow block diagram of one embodiment of the method of programming the reservoirs and dispense logic using one or more algorithms using the computing component 1600. FIG. 17 shows the user information and data relating to the medication may be transmitted to and from an automated medication adherence system 1610, by one or more health care providers 1615, and/or pharmacists 1620 through an online connection, bar code scan, or direct upload. For example, the electronic interface 1625 may be manually programmed with data relating to the medication, including a pill identity, pill type, pill size, pill shape, pill images, schedule time, daily frequency, a user identity, a dosage schedule, dosage information, not to exceed amounts, instructions for use and potential side effects. The electronic interface 1625 may enable programming of each of the reservoirs with the specific information about the medication to be held in the respective reservoir. Additionally, the electronic interface may utilize a bar code reader, positioned on the exterior of the automated medication adherence system 1610, or at another appropriate location, to read the medication prescription record number and other bar-coded information needed for automatic programming and ease of use by a user 1605 of the automated medication adherence system 1610. For example, the bar code reader may enable the recognition of data relating to the medication, including a pill identity, pill type, pill size, pill shape, a user identity, a dosage schedule, dosage information, and potential side effects. Therefore, the automated medication adherence system 1610 does not require any programming by a user 1605. Prior to loading medication into a reservoir, the bar code reader may allow the user 1605 to send data relating to the medication to the electronic interface 1625 for programming each of the reservoirs with specific information about the medication to be loaded.

The data relating to the medication may be stored in a cloud application 1630. The cloud application 1630 may also receive data relating to the medication from a pharmacy software interface 1635. When a health care provider 1615 writes a prescription for the user 1605, the prescription may be stored in a health care provider software interface 1640 and transmitted as an e-prescription 1645 to the pharmacy software interface 1635. The pharmacy software interface 1635 may work in conjunction with a pharmacist 1620 to dispatch the appropriate medication for the user 1605. Additionally, the pharmacy software interface 1635 may transmit the e-prescription 1645 to the cloud application 1630 for programming the electronic interface 1625 of the automated medical adherence system 1610. Data relating to the medication may also be stored in a medication database 1655.

FIG. 17 also shows that the automated medication adherence system 1610 may be in communication with a health care provider 1615 to allow the health care provider 1615 to perform various modifications to the programming of the automated medication adherence system 1610 from a remote location. Additionally, this communication may alert a health care provider 1615 to problems, such as when the user 1605 fails to remove one or more dosages of medication from the pill delivery and lock-out module. Communication is preferably achieved by sending and receiving medication events 1650 via a cloud application 1630.

Unless otherwise stated, all measurements, values, ratings, positions, magnitudes, sizes, locations, and other specifications that are set forth in this specification, including in the claims that follow, are approximate, not exact. They are intended to have a reasonable range that is consistent with the functions to which they relate and with what is customary in the art to which they pertain.

The foregoing description of the preferred embodiment has been presented for the purposes of illustration and description. While multiple embodiments are disclosed, still other embodiments will become apparent to those skilled in the art from the above detailed description. The disclosed embodiments capable of modifications in various obvious aspects, all without departing from the spirit and scope of the protection. Accordingly, the detailed description is to be regarded as illustrative in nature and not restrictive. Also, although not explicitly recited, one or more embodiments may be practiced in combination or conjunction with one another. Furthermore, the reference or non-reference to a particular embodiment shall not be interpreted to limit the scope. It is intended that the scope or protection not be limited by this detailed description, but by the claims and the equivalents to the claims that are appended hereto.

Unless otherwise stated, all measurements, values, ratings, positions, magnitudes, sizes, locations, and other specifications that are set forth in this specification, including in the claims that follow, are approximate, not exact. They are intended to have a reasonable range that is consistent with the functions to which they relate and with what is customary in the art to which they pertain.

The foregoing description of the preferred embodiment has been presented for the purposes of illustration and description. While multiple embodiments are disclosed, still other embodiments will become apparent to those skilled in the art from the above detailed description. These embodiments are capable of modifications in various obvious aspects, all without departing from the spirit and scope of protection. Accordingly, the detailed description is to be regarded as illustrative in nature and not restrictive. Also, although not explicitly recited, one or more embodiments may be practiced in combination or conjunction with one another. Furthermore, the reference or non-reference to a particular embodiment shall not be interpreted to limit the scope of protection. It is intended that the scope of protection not be limited by this detailed description, but by the claims and the equivalents to the claims that are appended hereto.

Except as stated immediately above, nothing that has been stated or illustrated is intended or should be interpreted to cause a dedication of any component, step, feature, object, benefit, advantage, or equivalent, to the public, regardless of whether it is or is not recited in the claims.

What is claimed is:

1. An automated medication adherence system, comprising:
 a housing;
 an electronic interface; and
 one or more of sensors;
 wherein said housing comprises a pill delivery and lock-out module;
 wherein said housing is configured to contain a plurality of reservoirs;
 wherein said plurality of reservoirs are configured for receiving, storing, and dispensing one or more medications;
 wherein said housing comprises an access cover;
 wherein said housing comprises a reservoir loading door;
 wherein said access cover comprises a pill loading assembly;
 wherein said pill loading assembly is configured to allow said one or more medications to be loaded into at least one of said plurality of reservoirs;
 wherein said reservoir loading door comprises a reservoir loading assembly;

wherein said reservoir loading door is configured to allow said one or more reservoirs to be loaded and locked into a rotating carrier;

wherein said electronic interface comprises a computing component and at least one display component;

wherein said electronic interface is on an exterior portion of said housing;

wherein said electronic interface is programmable, such that said electronic interface accepts data relating to said one or more medications;

wherein each of said plurality of reservoirs is configured to receive, store and dispense a homogenous type of medication of said one or more medications;

wherein each of said plurality of reservoirs comprises two successive stages, a first stage and a second stage;

wherein said two successive stages are configured to be stacked, such that said first stage is substantially above said second stage;

wherein each of said two successive stages comprises an opening, such that there are two openings, a first opening and a second opening;

wherein said first opening and said second opening are selectively openable and closable in response to said electronic interface;

wherein each of said two successive stages receive and dispense said one or more medications through said two openings;

wherein each of said plurality of reservoirs comprises a central agitation stalk, an outer wall; an inner wall; and one or more actuators;

wherein said central agitation stalk is configured to be substantially contained within said inner wall, and wherein said inner wall is configured to be substantially contained within said outer wall;

wherein said central agitation stalk is configured to be rotatable within said inner wall;

wherein said central agitation stalk comprises a fin portion, a wave surface, and a ribbed cone surface;

wherein said fin portion comprises a plurality of fins that are configured to prevent said one or more medications from clumping together;

wherein said wave surface is a base of said first stage;

wherein said ribbed cone surface is a base of said second stage;

wherein said one or more medications are moved from said first stage to said second stage and then from said second stage to said pill delivery and lock-out module;

wherein said one or more medications are a plurality of pills; and wherein each of one or more sensors are connected with said computing component;

wherein said one or more sensors are configured to determine when a single pill of said plurality of pills passes through each of said two successive stages.

2. The automated medication adherence system of claim 1, further comprising:
a rotating carrier;
wherein said rotating carrier is configured to engage with said plurality of reservoirs, such that said plurality of reservoirs are configured to rotate within said housing.

3. The automated medication adherence system of claim 2, wherein said electronic interface rotates said plurality of reservoirs in response to said data relating to said one or more medications.

4. The automated medication adherence system of claim 1, wherein said data relating to said one or more medications is selected from the group of data consisting of: a pill identity; a user identity; a dosage schedule; a medication format; a pill image; a plurality of pharmaceutical indications for use; instructions for use; a physical description; a chemical description; a refill information; and a plurality of side effect information.

5. The automated medication adherence system of claim 1, wherein said one or more actuators are configured to rotate and agitate said central agitation stalk and at least one of said inner wall and said outer wall.

6. The automated medication adherence system of claim 5, wherein said outer wall comprises one or more outer wall portholes and one or more chutes;
wherein said inner wall comprises one or more inner wall portholes;
wherein at least one of said one or more actuators is configured to rotate at least one of said inner wall and said outer wall, such that said inner wall and said outer wall are rotated with respect to each other;
wherein when said inner wall and said outer wall are rotated with respect to each other, said one or more outer wall portholes and said one or more inner wall portholes align to form said two openings;
wherein said computing component comprises one or more logic algorithms;
wherein said one or more sensors, said one or more actuators, and said one or more logic algorithms are configured to control said inner wall, said outer wall, and said central agitation stalk to ensure that said one or more medications are transferred, one pill at a time, from said first stage to said second stage; and
wherein said one or more sensors, said one or more actuators, and said one or more logic algorithms are configured to control said inner wall, said outer wall, and said central agitation stalk to ensure that said one or more medications are transferred, one pill at a time, from said second stage to said pill delivery and lock-out module.

7. The automated medication adherence system of claim 6, wherein said electronic interface alerts a user when said one or more medications are dispensed, such that a dispensed medication is created.

8. The automated medication adherence system of claim 7, wherein said electronic interface alerts one or more of said user, one or more authorized individuals, and one or more health care providers when said user has not removed said dispensed medication from said pill delivery and lock-out module in accordance with said data relating to said one or more medications.

9. The automated medication adherence system of claim 8, wherein said pill delivery and lock-out module comprises a holding tray, a dispensing tray, and a lock-out module;
wherein said lock-out module opens and accepts said dispensed medication not removed from said pill delivery and lock-out module or dispensed medication that was incorrectly dispensed;
wherein said access cover is configured to have closed and opened positions; and
wherein said plurality of reservoirs are accessible when said access cover is in said opened position for purposes of maintenance.

10. An automated medication adherence system, comprising:
a housing;
an electronic interface;
a rotating carrier;
wherein said housing comprises a pill delivery and lock-out module;

wherein said housing is configured to contain a plurality of reservoirs;

wherein said plurality of reservoirs are configured for receiving, storing, and dispensing one or more medications;

wherein said rotating carrier is configured to engage with said plurality of reservoirs, such that said plurality of reservoirs are configured to rotate within said housing;

wherein said housing comprises an access cover;

wherein said housing comprises a reservoir loading door;

wherein said access cover is configured to have closed and opened positions;

wherein said plurality of reservoirs are accessible when said access cover is in said opened position;

wherein said access cover comprises a pill loading assembly;

wherein said pill loading assembly is configured to allow said one or more medications to be loaded into at least one of said plurality of reservoirs;

wherein said reservoir loading door comprises a reservoir loading assembly;

wherein said reservoir loading door is configured to allow said one or more reservoirs to be loaded and locked into a rotating carrier;

wherein said electronic interface comprises a computing component and at least one display component;

wherein said electronic interface is on an exterior portion of said housing;

wherein said electronic interface is programmable, such that said electronic interface accepts data relating to said one or more medications;

wherein said data relating to said one or more medications is selected from the group of data consisting of: a pill identity; a user identity; a dosage schedule; a medication format; a pill image; a plurality of pharmaceutical indications for use; instructions for use; a physical description; a chemical description; a refill information; and a plurality of side effect information;

wherein said electronic interface rotates said plurality of reservoirs in response to said data relating to said one or more medications;

wherein each of said plurality of reservoirs is configured to receive, store and dispense a homogenous type of said medication;

wherein each of said plurality of reservoirs comprises one or more sensors and two successive stages, a first stage and a second stage;

wherein said medication is moved from said first stage to said second stage and then from said second stage to said pill delivery and lock-out module;

wherein said two successive stages are configured to be stacked, such that said first stage is substantially above said second stage;

wherein each of said two successive stages comprises an opening, such that there are two openings, a first opening and a second opening;

wherein said first opening and said second opening are selectively openable and closable in response to said electronic interface;

wherein each of said two successive stages receives and dispenses said medication through said two openings;

wherein said medication is a plurality of pills;

wherein said one or more sensors are configured to determine when a single pill of said plurality of pills passes through each of said two openings;

wherein each of said plurality of reservoirs comprises a central agitation stalk, an outer wall, an inner wall, and one or more actuators;

wherein said central agitation stalk is configured to be substantially contained within said inner wall, and wherein said inner wall is configured to be substantially contained within said outer wall;

wherein said central agitation stalk is configured to be rotatable within said inner wall;

wherein said central agitation stalk comprises a fin portion, a wave surface, and a ribbed cone surface;

wherein said fin portion comprises a plurality of fins that are configured to prevent said medication from clumping together;

wherein said wave surface is a base of said first stage;

wherein said ribbed cone surface is a base of said second stage;

wherein said central agitation stalk is configured to engage with at least one of said one or more actuators in order to be rotated;

wherein said central agitation stalk comprises a plurality of gear teeth, which are configured to be engaged with at least one of said one or more actuators;

wherein said one or more actuators are configured to rotate said central agitation stalk and at least one of said inner wall and said outer wall;

wherein said one or more actuators are configured to agitate said central agitation stalk and at least one of said inner wall and said outer wall;

wherein said outer wall comprises one or more outer wall portholes and one or more chutes;

wherein said inner wall comprises one or more inner wall portholes;

wherein at least one of said one or more actuators are configured to rotate at least one of said inner wall and said outer wall, such that said inner wall and said outer wall are rotated with respect to each other;

wherein when said inner wall and said outer wall are rotated with respect to each other, said one or more outer wall portholes and said one or more inner wall portholes align to form said two openings;

wherein said computing component comprises one or more logic algorithms;

wherein said one or more sensors, said one or more actuators, and said one or more logic algorithms are configured to control said inner wall, said outer wall, and said central agitation stalk to ensure that said medication is transferred, a set number of pills at a time, from said first stage to said second stage; and wherein said one or more sensors, said one or more actuators, and said one or more logic algorithms are configured to control said inner wall, said outer wall, and said central agitation stalk to ensure that said medication is transferred, one pill at a time, from said second stage to said pill delivery and lock-out module.

* * * * *